US010220091B2

(12) United States Patent
Sabbatino et al.

(10) Patent No.: US 10,220,091 B2
(45) Date of Patent: Mar. 5, 2019

(54) COMBINATION TREATMENTS WITH SONIC HEDGEHOG INHIBITORS

(71) Applicant: The General Hospital Corporation, Boston, MA (US)

(72) Inventors: Francesco Sabbatino, Boston, MA (US); Yangyang Wang, Malden, MA (US); Xinhui Wang, Boston, MA (US); Steven Isakoff, Brookline, MA (US); Cristina Ferrone, Boston, MA (US); Joe Schwab, Boston, MA (US); Soldano Ferrone, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/782,260

(22) PCT Filed: Apr. 3, 2014

(86) PCT No.: PCT/US2014/032762
§ 371 (c)(1),
(2) Date: Oct. 2, 2015

(87) PCT Pub. No.: WO2014/165644
PCT Pub. Date: Oct. 9, 2014

(65) Prior Publication Data
US 2016/0045598 A1    Feb. 18, 2016

Related U.S. Application Data

(60) Provisional application No. 61/808,517, filed on Apr. 4, 2013.

(51) Int. Cl.
*A61K 45/06* (2006.01)
*A61K 31/437* (2006.01)
*A61K 39/395* (2006.01)
*A61K 31/5377* (2006.01)

(52) U.S. Cl.
CPC ...... *A61K 39/39558* (2013.01); *A61K 31/437* (2013.01); *A61K 31/5377* (2013.01); *A61K 45/06* (2013.01); *C12N 2740/15043* (2013.01)

(58) Field of Classification Search
None
See application file for complete search history.

(56) References Cited

U.S. PATENT DOCUMENTS

| 2012/0009194 | A1 | 1/2012 | Ferrone et al. | |
|---|---|---|---|---|
| 2012/0010229 | A1* | 1/2012 | MacDougall | A61K 31/00 514/278 |
| 2012/0010230 | A1* | 1/2012 | MacDougall | A61K 31/4355 514/278 |
| 2012/0148598 | A1 | 6/2012 | Ferrone et al. | |

FOREIGN PATENT DOCUMENTS

| WO | WO 2007/084560 | 7/2007 | |
|---|---|---|---|
| WO | WO-2011090738 A2 * | 7/2011 | ........... C07D 487/04 |
| WO | WO 2012/159085 | 11/2012 | |

OTHER PUBLICATIONS

Fedorenko et al (Biochemical Pharmacology 2011, 82:201-209).*
Stecca et al. (PNAS Apr. 3, 2007, 104(14): 5895-590).*
Garg et al. (J. Invest. Med. Jan. 2012 60(1): 147 Ab. No. 76 (Year: 2012).*
Singh et al. (PLoS ONE Nov. 2011 6 (11): e277306, 11 pages) (Year: 2011).*
Li et al. (Mol. Cell Biochem. Nov. 6, 2012, 373:217-227) (Year: 2012).*
Ruch and Kim, "Hedgehog Signaling Pathway and Cancer Therapeutics: Progress to Date," Drugs, May 2013, 73(7)613-623.
Agaimy et al., "V600E BRAF mutations are alternative early molecular events in a subset of KIT/PDGFRA wild-type gastrointestinal stromal tumours," Journal of Clinical Pathology, 2009, 62: 613-616.
Agaram et al., "Novel V600E BRAF mutations in imatinib-naïve and imatinib-resistant gastrointestinal stromal tumors," Genes, Chromosomes & Cancer, Oct. 2008, 47: 853-859.
Akutsu, "Combination of direct intratumoral administration of dendritic cells and irradiation induces strong systemic antitumor effect mediated by grp94/gp96 against squamous cell carcinoma in mice," International Journal of Oncology, Sep. 2007, 31: 509-515.
Ginestier et al., "ALDH1 Is a Marker of Normal and Malignant Human Mammary Stem Cells and a Predictor of Poor Clinical Outcome," Cell Stem Cell, Nov. 2007; 1:555-567.
Andrae et al., "Role of platelet-derived growth factors in physiology and medicine," Genes & Development, 2008, 22: 1276-1312.
Argon and Simen, "Grp94, an ER chaperone with protein and peptide binding properties," Seminars in Cell & Developmental Biology, 1999,10:495-505.
Atefi et al. "Reversing melanoma cross-resistance to BRAF and MEK inhibitors by co-targeting the AKT/mTOR pathway," PLoS One, Dec. 20116: e28973.
Brose et al., "BRAF and RAS mutations in human lung cancer and melanoma," Cancer Research, Dec. 2002, 62: 6997-7000.
Buchdunger et al., "Inhibition of the Abl protein-tyrosine kinase in vitro and in vivo by a 2-phenylaminopyrimidine derivative," Cancer Research, Jan. 1996, 56: 100-104.
Chapman et al., "Improved survival with vemurafenib in melanoma with BRAF V600E mutation," N Engl J Med, 2011, 364: 2507-2516.
Chappell et al., "Ras/Raf/MEK/ERK and PI3K/PTEN/ Akt/mTOR inhibitors: rationale and importance to inhibiting these pathways in human health," Oncotarget, 2011, 2: 135-164.

(Continued)

*Primary Examiner* — Peter J Reddig
(74) *Attorney, Agent, or Firm* — Fish & Richardson P.C.

(57) ABSTRACT

Methods for treating cancer using a combination of an inhibitor of the sonic hedgehog signaling pathway (e.g., LDE225) with radiation and a tumor antigen-specific monoclonal antibody (e.g., heat shock protein (HSP) glucose regulated protein of 94000 daltons (Grp94)-specific mAb W9, or chondroitin sulfate proteoglycan 4 (CSPG4)-targeted mAbs), or with a BRAF inhibitor, e.g., in BRAF inhibitor resistant cancers.

3 Claims, 15 Drawing Sheets
Specification includes a Sequence Listing.

(56) References Cited

OTHER PUBLICATIONS

Cheung et al., "Akt3 and mutant V600E B-Raf cooperate to promote early melanoma development," Cancer Research, May 2008, 68: 3429-3439.
Chow and Eckhardt, "Sunitinib: from rational design to clinical efficacy," Journal of Clinical Oncology, Mar. 2007, 25: 884-896.
Clarke et al., "Cancer stem cells—perspectives on current status and future directions: AACR workshop on cancer stem cells," Cancer Res., Oct. 2006, 66:9339-9344.
Cohen et al., "Mitogen-activated protein kinase activation is an early event in melanoma progression," Clin Cancer Res, Dec. 2002, 8: 3728-3733.
Corcoran et al., "BRAF gene amplification can promote acquired resistance to MEK inhibitors in cancer cells harboring the BRAF V600E mutation," Science Signaling, 2010, 3: ra84.
Deng et al., "Role and therapeutic potential of PI3K-mTOR signaling in de novo resistance to BRAF inhibition," Pigment Cell & Melanoma Research, Mar. 2012, 25: 248-258.
Dormoy et al., "The sonic hedgehog signaling pathway is reactivated in human renal cell carcinoma and plays orchestral role in tumor growth," Molecular Cancer, 2009, 8:123.
Elia et al., "Sonic hedgehog promotes proliferation and differentiation of adult muscle cells: Involvement of mapk/erk and pi3k/akt pathways," Biochimica et Biophysica Acta, Sep. 2007, 1773:1438-1446.
Emery et al., "MEK1 mutations confer resistance to MEK and BRAF inhibition," PNAS, Dec. 2009,106: 20411-20416.
Fendrich et al., "Hedgehog inhibition with the orally bioavailable Smo antagonist LDE225 represses tumor growth and prolongs survival in a transgenic mouse model of islet cell neoplasms," Annals of Surgery, Nov. 2011, 254:818-823.
Flaherty et al, "Combined BRAF and MEK inhibition in melanoma with BRAF V600 mutations," The New England Journal of Medicine, 2012, 367: 1694-1703.
Flaherty et al., "Inhibition of mutated, activated BRAF in metastatic melanoma," The New England Journal of Medicine, 2010, 363: 809-819.
Greger et al., "Combinations of BRAF, MEK, and PI3K/mTOR inhibitors overcome acquired resistance to the BRAF inhibitor GSK2118436 dabrafenib, mediated by NRAS or MEK mutations," Molecular Cancer Therapeutics, 2012, 11: 909-920.
Hostein et al., "BRAF mutation status in gastrointestinal stromal Tumors," American Journal of Clinical Pathology, 2010, 133: 141-148.
International Preliminary Report on Patentability and Written Opinion of the International Searching Authority in International Application No. PCT/US2014/32762, dated Oct. 6, 2015, 8 pages.
Irvine and Copland, "Targeting hedgehog in hematologic Malignancy," Blood, 2012;119:2196-2204.
Ji et al., "Oncogenic kras activates hedgehog signaling pathway in pancreatic cancer cells," The Journal of Biological Chemistry, May 2007, 282:14048-1405.
Johannessen et al., "COT/MAP3K8 drives resistance to RAF inhibition through MAP kinase pathway reactivation," Nature, Dec. 2010, 468: 968-972.
Kameda et al, "The hedgehog pathway is a possible therapeutic target for patients with estrogen receptor-negative breast cancer," Anticancer Research, 2009, 29:871-879.
Karasarides et al., "B-RAF is a therapeutic target in melanoma," Oncogene, 2004, 23: 6292-6298.
Kelleher, Hedgehog signaling and therapeutics in pancreatic Cancer, Carcinogenesis, 2011, 32:445-451.
Kim et al., "ALDH activity selectively defines an enhanced tumor-initiating cell population relative to CD133 expression in human pancreatic adenocarcinoma," PloS One, Jun. 2011, 6:e20636.
Lauth, "Ras and hedgehog—partners in crime," Frontiers in Bioscience, Jun. 2011, 16:2259-2270.
Li et al., "Identification of pancreatic cancer stem cells," Cancer Res., 2007, 67:1030-1037.

Liu et al., "Enhancement of cancer radiation therapy by use of adenovirus-mediated secretable glucose-regulated protein 94/gp96 expression," Cancer Res., 2005, 65:9126-9131.
Long et al., "Prognostic and clinicopathologic associations of oncogenic BRAF in metastatic melanoma," J Clin Oncol, Apr. 2011, 29: 1239-1246.
Lopez-Bergami, "The role of mitogen- and stress-activated protein kinase pathways in melanoma," Pigment Cell Melanoma Res, 2011, 24: 902-921.
Marzec et al., Grp94: An hsp90-like protein specialized for protein folding and quality control in the endoplasmic reticulum, Biochiln Biophys Acta., Mar. 2012, 1823:774-787.
Miranda et al., "KRAS and BRAF mutations predict primary resistance to imatinib in gastrointestinal stromal tumors," Clinical Cancer Research, 2012, 18: 1769-1776.
Montagut et al., "Elevated CRAF as a potential mechanism of acquired resistance to BRAF inhibition in melanoma," Cancer Research, Jun. 2008, 68: 4853-4861.
Nazarian et al., "Melanomas acquire resistance to B-RAF(V600E) inhibition by RTK or N-RAS upregulation," Nature, Dec. 2010, 468: 973-977.
Ogino et al., "Endoplasmic reticulum chaperone-specific monoclonal antibodies for flow cytometry and immunohistochemical staining," Tissue Antigens, Nov. 2003, 62: 385-393.
Ohashi et al., "Discovery of the investigational drug TAK-441, a pyrrolo[3,2-c]pyridine derivative, as a highly potent and orally active hedgehog signaling inhibitor: modification of the core skeleton for improved solubility," Bioorg Med Chem., Sep. 2012, 20(18):5507-17.
Olive et al., "Inhibition of hedgehog signaling enhances delivery of chemotherapy in a mouse model of pancreatic cancer," Science, Jun. 2009, 324: 1457-1461.
Pan et al., "Silencing of grp94 expression promotes apoptosis in pancreatic cancer cells," International Journal of Oncology, Jun. 2009, 35:823-828.
Pan et al., "Discovery of nvp-lde225, a potent and selective smoothened antagonist," ACS Med. Chem. Lett, 2010, 1:130-134.
Paraiso et al., "PTEN loss confers BRAF inhibitor resistance to melanoma cells through the suppression of BIM expression," Cancer Res, Apr. 2011, 71: 2750-2760.
Poulikakos et al., "RAF inhibitor resistance is mediated by dimerization of aberrantly spliced BRAF(V600E)," Nature, Jun. 2012, 480: 387-390.
Quint et al., "Pancreatic cancer cells surviving gemcitabine treatment express markers of stem cell differentiation and epithelial-mesenchymal transition," International Journal of Oncology, Dec. 2012, 41: 2093-2102.
Rasheed and Matsui, "Biological and clinical relevance of stem cells in pancreatic adenocarcinoma," Journal of Gastroenterology and Hepatology, Mar. 2012, 27(Suppl 2):15-18.
Romer and Curran, "Targeting Medulloblastoma: Small-Molecule Inhibitors of the Sonic Hedgehog Pathway as Potential Cancer Therapeutics," Cancer Res, Jun. 15, 2005 65: 4975-4978.
Ross et al., "Anticancer Antibodies," Am J Clin Pathol, Apr. 2003, 119(4):472-485.
Ruiz i Altaba et al., "The Gli code: an information nexus regulating cell fate, stemness and cancer," Trends in Cell Biology, Sep. 2007, 17: 438-447.
Ruiz i Altaba et al., Gli and hedgehog in cancer: tumours, embryos and stem cells, Nature Reviews, May 2002, 2: 361-372.
Sanchez-Hernandez et al., "Dual inhibition of V600EBRAF and the PI3K/AKT/mTOR pathway cooperates to induce apoptosis in melanoma cells through a MEK-independent mechanism," Cancer Letters, Jan. 2012, 314: 244-255.
Shi et al., "Combinatorial treatments that overcome PDGFRbeta-driven resistance of melanoma cells to V600EB-RAF inhibition," Cancer Research, 2011, 71: 5067-5074.
Sosman et al., "A phase 2 trial of complete resection for stage IV melanoma: Results of Southwest Oncology Group Clinical Trial S9430," Cancer, Mar. 2011, 117: 4740-4706.
Stecca et al., "Melanomas require HEDGEHOG-GLI signaling regulated by interactions between GLI1 and the RAS-MEK/ AKT pathways," PNAS, Apr. 2007, 104: 5895-5900.

(56) References Cited

OTHER PUBLICATIONS

Straussman et al., "Tumor micro-environment elicits innate resistance to RAF inhibitors through HGF secretion," Nature, Jul. 2012, 487: 500-504.
Su et al., "Resistance to selective BRAF inhibition can be mediated by modest upstream pathway activation," Cancer Res, 2012, 72: 969-978.
Tang et al, "Bioenergetic metabolites regulate base excision repair dependent cell death in response to DNA damage," Molecular Cancer Research, Jan. 2010, 8: 67-79.
Tao et al., "Overexpression of hedgehog signaling molecules and its involvement in triple-negative breast cancer," Oncology Letters, Jul. 2011, 2:995-1001.
Van Hoff et al., "Inhibition of the Hedgehog Pathway in Advanced Basal-Cell Carcinoma," N Engl J Med, Sep. 2009, 361: 1164-72.
Vermes et al., "A novel assay for apoptosis. Flow cytometric detection of phosphatidylserine expression on early apoptotic cells using fluorescein labelled Annexin V," Journal of Immunological Methods, 1995, 184: 39-51.
Villanueva et al., "Acquired resistance to BRAF inhibitors mediated by a RAF kinase switch in melanoma can be overcome by cotargeting MEK and IGF-1 R/PBK," Cancer Cell, Dec. 2010,18: 683-695.
Visus et al., "Targeting ALDH(bright) Human Carcinoma-Initiating Cells with ALDH1A1-Specific CD8Dþ T Cells," Clinical Cancer Research, Oct. 2011, 17:6174-6184.
Visvader, "Cells of origin in cancer," Nature, Jan. 2011, 469:314-322.
Wagle et al., "Dissecting therapeutic resistance to RAF inhibition in melanoma by tumor genomic profiling," Journal of Clinical Oncology, Aug. 2011, 29: 3085-3096.

Wan et al., "Mechanism of activation of the RAF-ERK signaling pathway by oncogenic mutations of B-RAF," Cell, Mar. 2004,116: 855-867.
Wang et al., "Cspg4 protein as a new target for the antibody-based immunotherapy of triple-negative breast cancer," Journal of the National Cancer Institute, Oct. 2010, 102:1496-1512.
Xie et al., "A role of PDGFRalpha in basal cell carcinoma Proliferation," PNAS, Jul. 2001, 98: 9255-9259.
Xu et al., "Genome-wide screening reveals an EMT molecular network mediated by sonic hedgehog-Glil signaling in pancreatic cancer cells," PloS One, Aug. 2012, 7:e43119.
Yang and Li, "Roles of heat shock protein gp96 in the ER quality control: Redundant or unique function?," Molecules and Cells, 2005, 20:173-182.
Yang et al, "RG7204 (PLX4032), a selective BRAFV600E inhibitor, displays potent antitumor activity in preclinical melanoma models," Cancer Research, Jul. 2010, 70: 5518-5527.
Yu et al, "The CSPG4-specific monoclonal antibody enhances and prolongs the effects of the BRAF inhibitor in melanoma cells," Immunol Res, Aug. 2011, 50: 294-302.
Zhang et al., "ER stress induced by ionising radiation in iec-6 cells," International Journal of Radiation Biology, 2010, 86:429-435.
Coon et al., "Molecular Therapy Targeting Sonic Hedgehog and Hepatocyte Growth Factor Signaling in a Mouse Model of Medulloblastoma," Mol. Cancer Ther., 2010, 9:2627-2636.
Evangelista et al., "The Hedgehog Signaling Pathway in Cancer," Clin. Cancer Res., 2006, 12:5924-5928.
International Search Report and Written Opinion in International Application No. PCT/US2014/32762, dated Sep. 26, 2014, 11 pages.

* cited by examiner

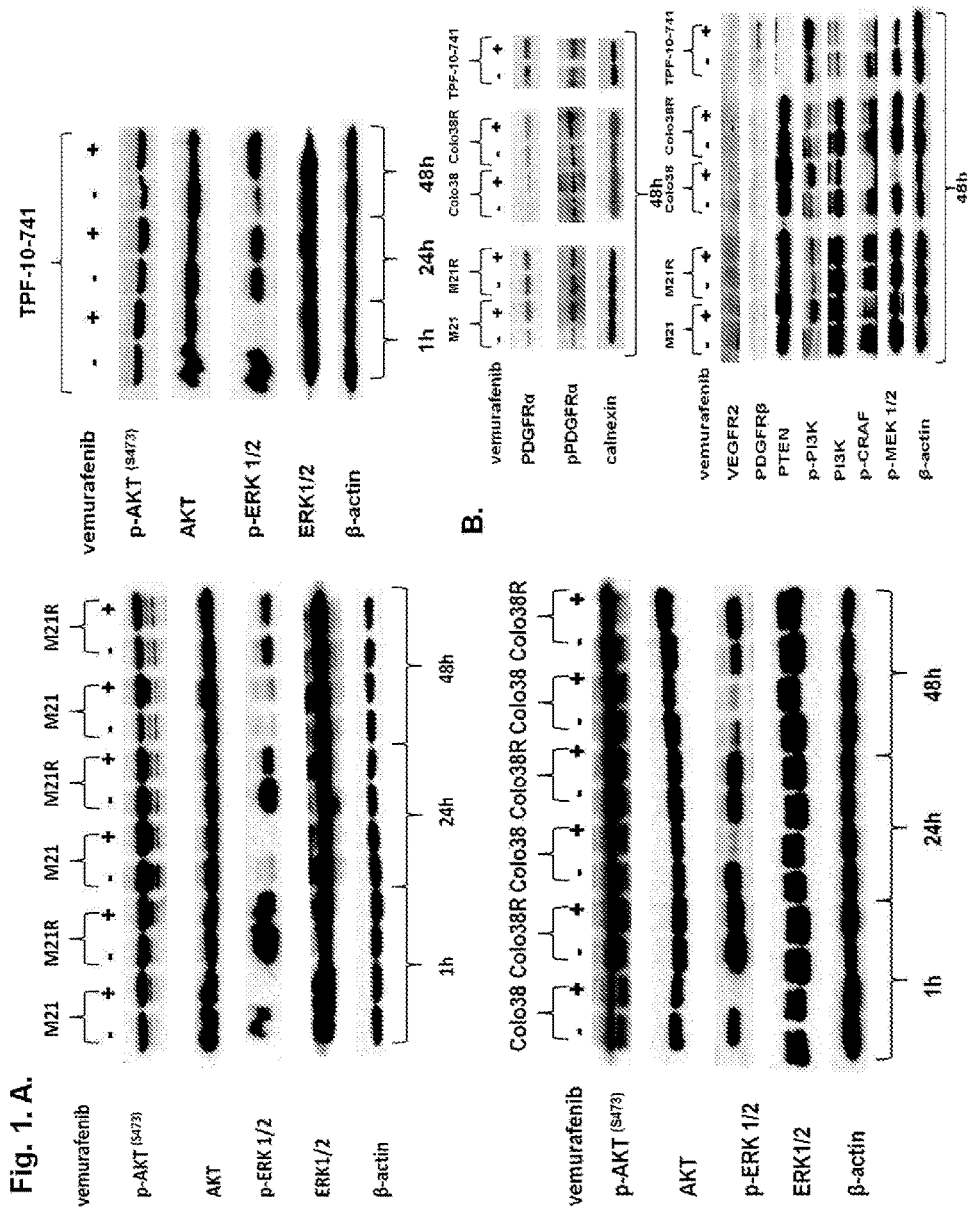
FIGs. 1A-B

A.
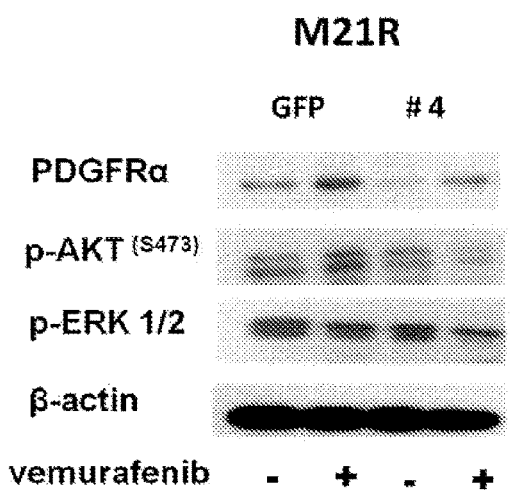
B.
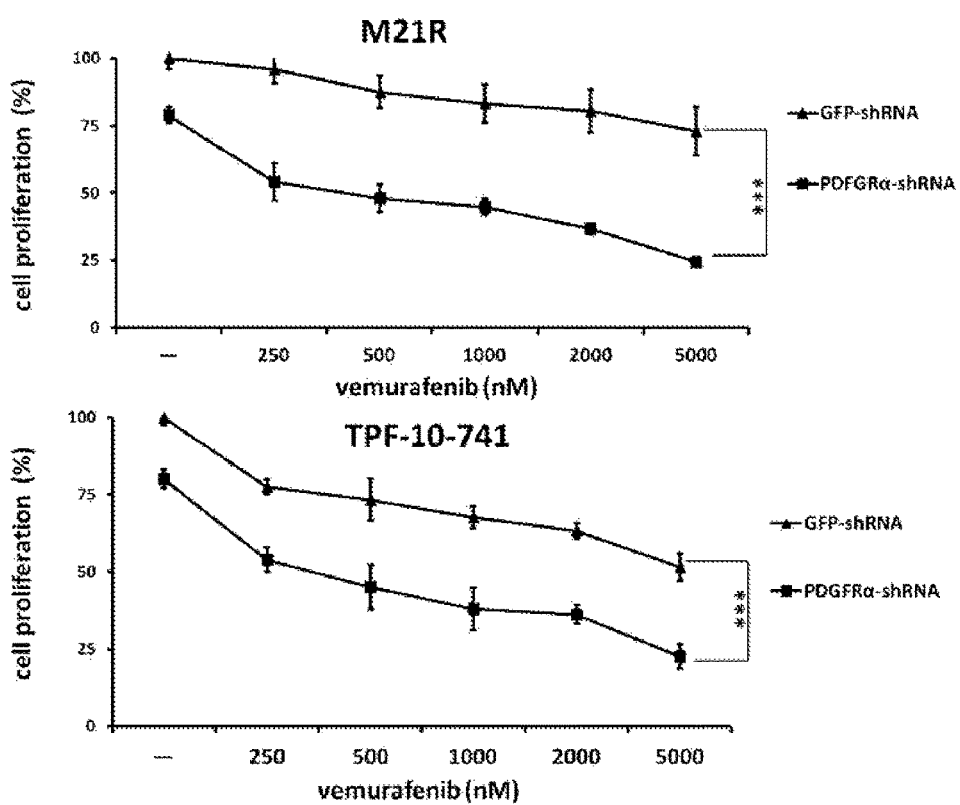
FIGs. 2A-B

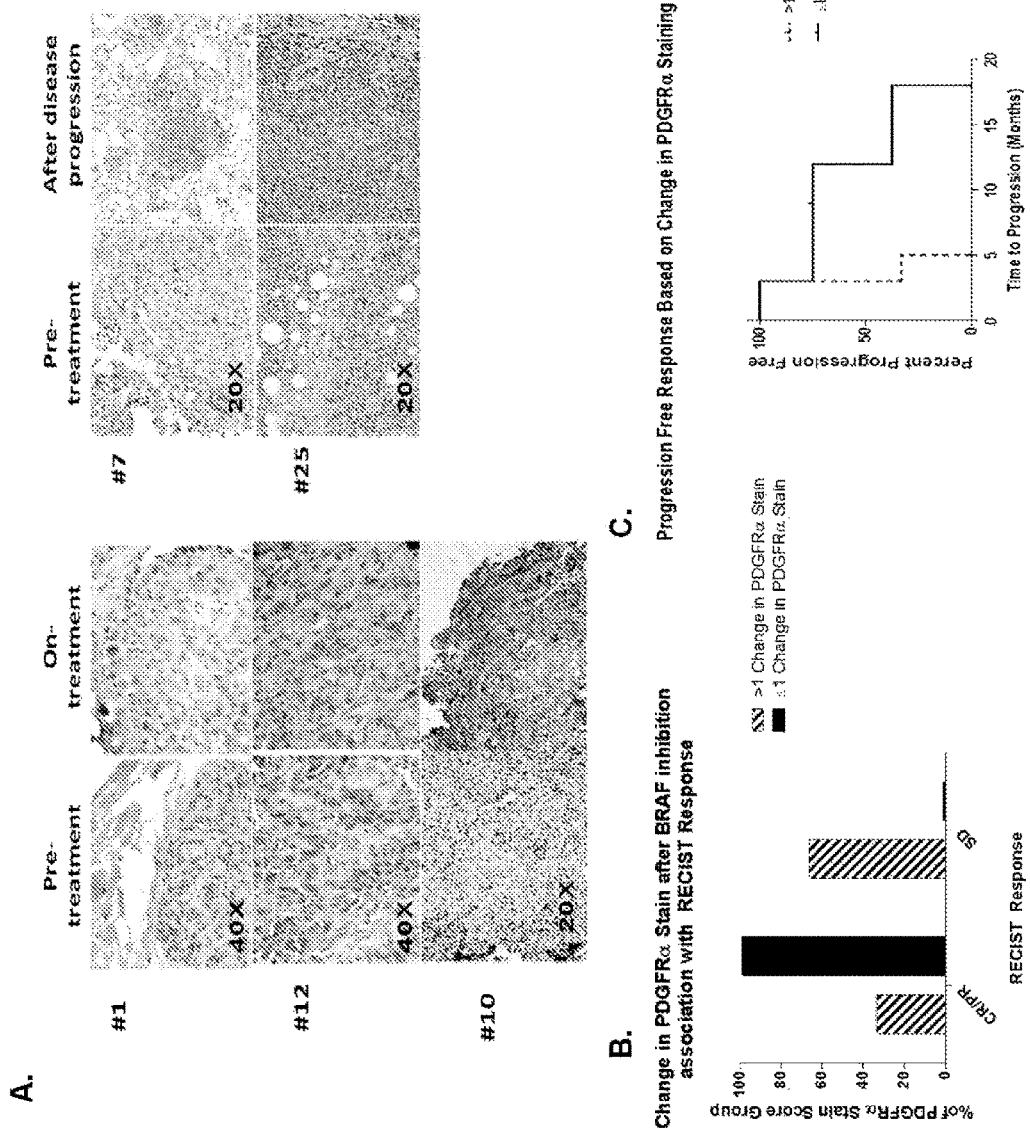
FIGs. 3A-C

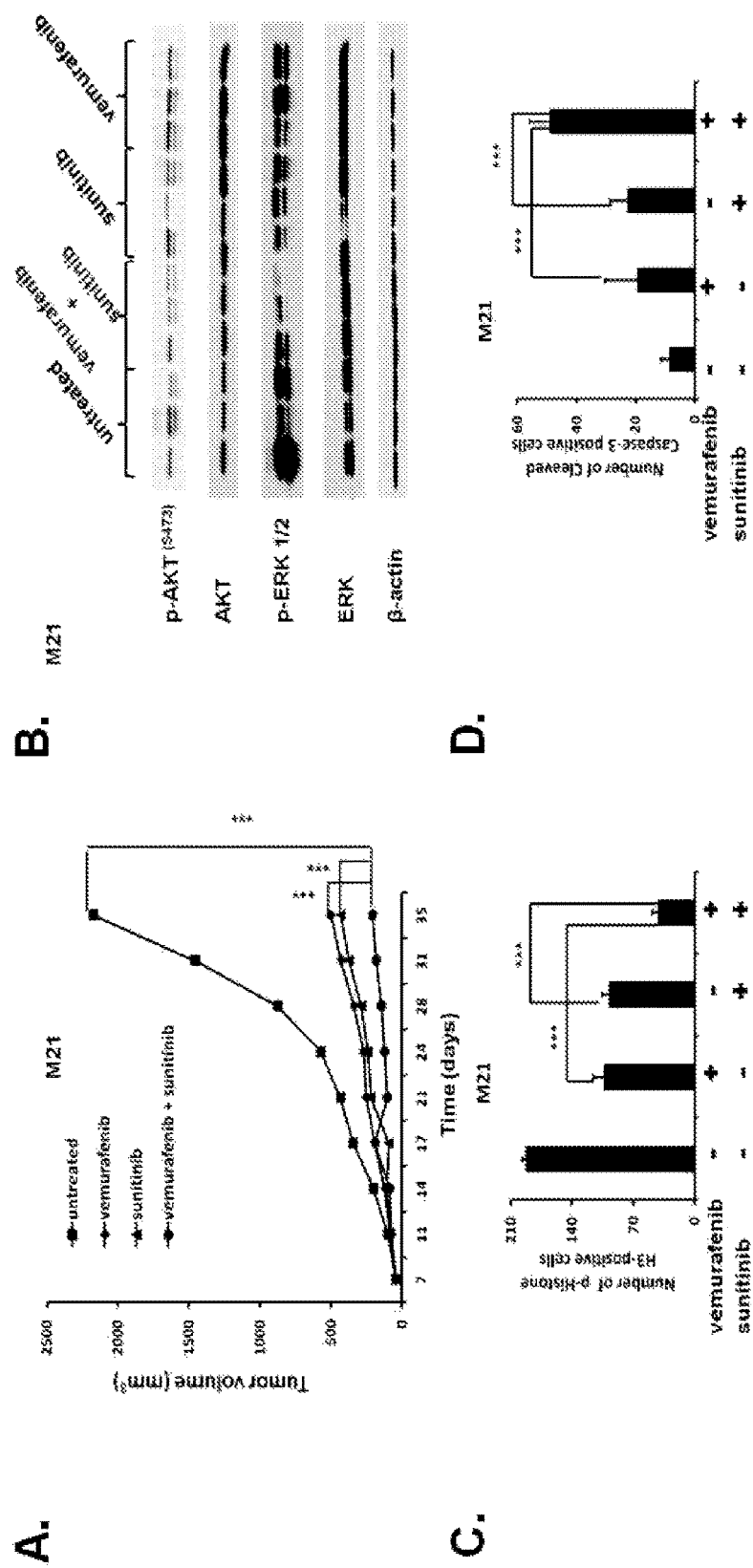
FIGs. 5A-D

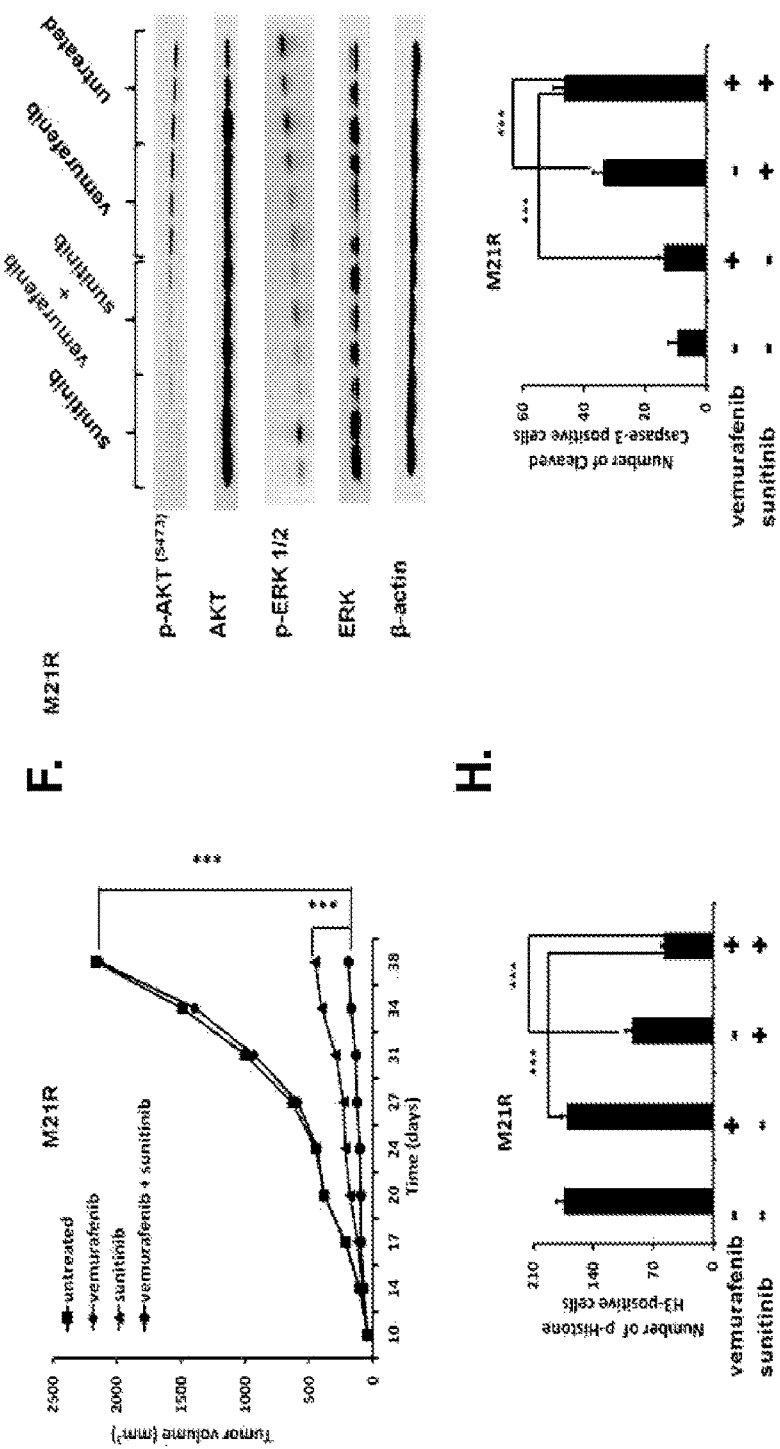
FIGs. 5E-H

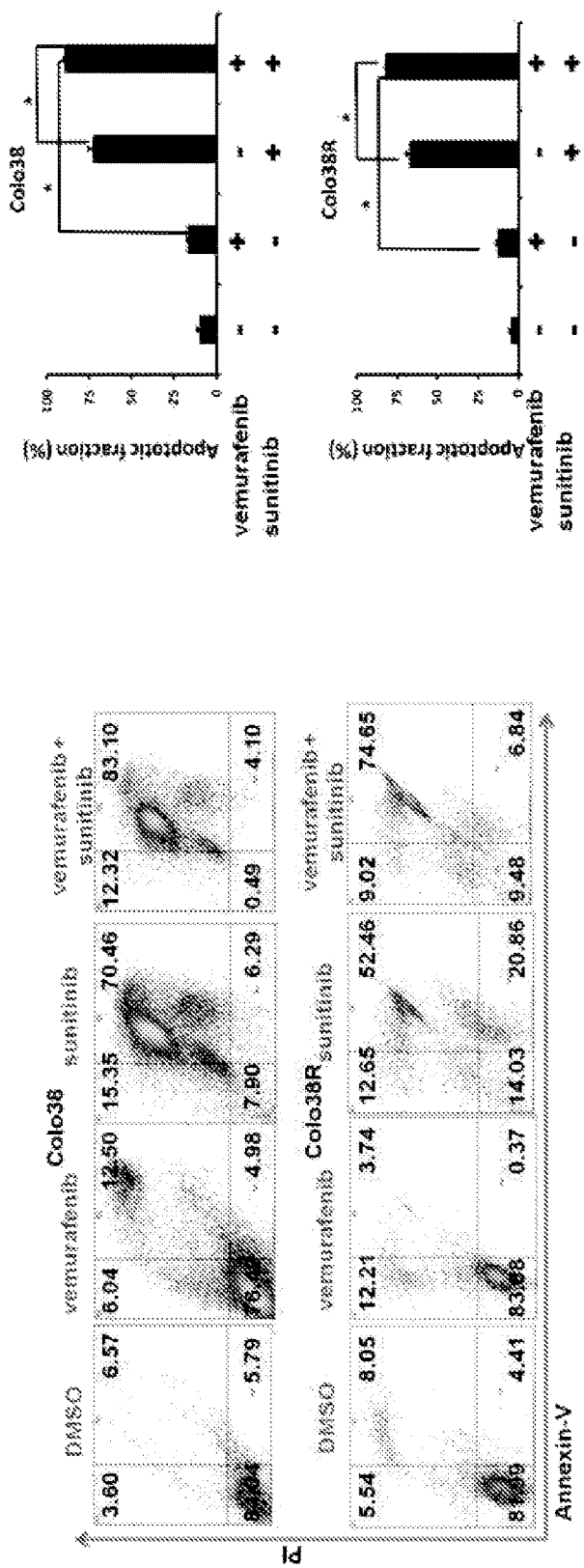
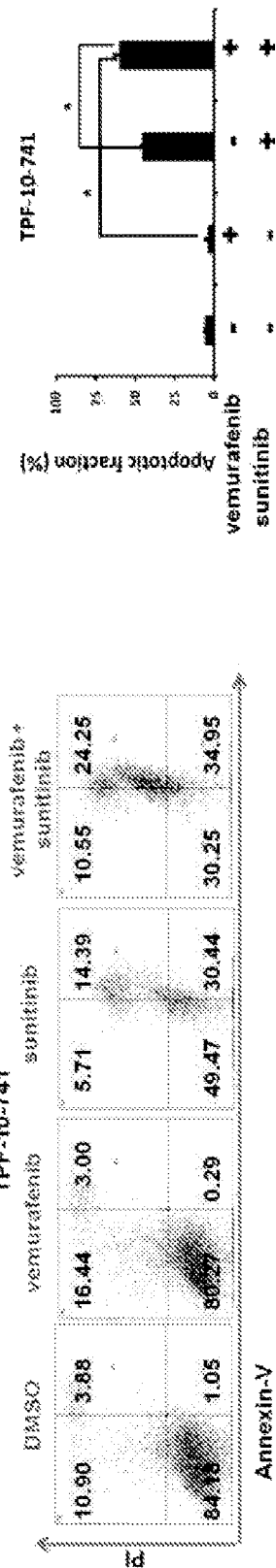
FIG. 10B
FIG. 10C

COMBINATION TREATMENTS WITH SONIC HEDGEHOG INHIBITORS

CLAIM OF PRIORITY

This application application is a U.S. National Phase Application under 35 U.S.C. § 371 of International Patent Application No. PCT/US2014/032762, filed on Apr. 3, 2014, which claims the benefit of U.S. Provisional Patent Application Ser. No. 61/808,517, filed on Apr. 4, 2013. The entire contents of the foregoing are hereby incorporated by reference.

FEDERALLY SPONSORED RESEARCH OR DEVELOPMENT

This invention was made with Government support under Grant Nos. RO1CA138188 and RO1CA110249 awarded by the National Cancer Institutes of the National Institutes of Health. The Government has certain rights in the invention.

REFERENCE TO SEQUENCE LISTING

The instant application contains a Sequence Listing which has been submitted electronically in ASCII format and is hereby incorporated by reference in its entirety. Said ASCII copy, created on Nov. 1, 2018, is named SL.txt and is 1,271 bytes in size.

TECHNICAL FIELD

The present application relates to methods for treating cancer using a combination of an inhibitor of the sonic hedgehog signaling pathway (e.g., LDE225) with a tumor antigen-specific monoclonal antibody (e.g., heat shock protein (HSP) glucose regulated protein of 94000 daltons (Grp94)-specific mAb W9, or chondroitin sulfate proteoglycan 4 (CSPG4)-targeted mAbs), or with a BRAF inhibitor, e.g., in BRAF inhibitor resistant cancers.

BACKGROUND

Combination therapies can enhance the effectiveness of certain treatments, boosting therapeutic efficacy of drugs that, alone, are not clinically useful, or providing new treatment modalities in drug resistant tumors.

SUMMARY

The present invention is based, at least in part, on the discovery that combining Sonic Hedgehog pathway inhibitors, e.g., LDE225, with one or more other treatments such as radiation, tumor-antigen specific monoclonal antibodies, PDGFRα inhibitors, and/or BRAF inhibitors, (BRAF-I) can synergistically increase treatment efficacy.

Thus, in a first aspect, the invention provides methods for treating BRAF inhibitor (BRAF-I)-resistant cancers, e.g., melanoma, sarcoma, or carcinoma, e.g., colon cancer, thyroid cancer, pancreatic adenocarcinoma, triple negative breast cancer, glioma, sarcoma, or melanoma, comprising administering a therapeutically effective amount of a BRAF-I and a Sonic Hedgehog Inhibitor (Shh-I). In some embodiments, the BRAF-I is selected from the group consisting of Vemurafenib, GDC-0879, PLX-4720, GSK2118436, Sorafenib Tosylate. dabrafenib, and LGX818.

In some embodiments of the methods described herein, instead of or in addition to the Shh-I, a PDGFRα inhibitor is used, e.g., Crenolanib (CP-868596); Ki8751; Ponatinib (AP24534); Nintedanib (BIBF 1120); Dovitinib (TKI-258, CHIR-258); Masitinib (AB1010); Imatinib (STI571); Pazopanib; or KRN 633.

In some embodiments of the methods described herein, the Shh-I is selected from the group consisting of sulforaphane; vismodegib; TAK-441; itraconazole; and erismodegib.

In another aspect, the invention provides methods for treating cancer, e.g., carcinoma, sarcoma, or melanoma, e.g., triple negative breast cancer or pancreatic ductal adenocarcinoma, comprising administering a therapeutically effective amount of an antibody that binds to a tumor antigen, and a Sonic Hedgehog Inhibitor (Shh-I). In some embodiments, the tumor antigen is Grp94 or chondroitin sulfate proteoglycan 4 (CSPG4).

In some embodiments, the cancer is a recurrent cancer, i.e., has recurred after treatment.

In some embodiments of the methods described herein, the Shh-I is selected from the group consisting of sulforaphane; vismodegib; TAK-441; itraconazole; and erismodegib.

In some embodiments of the methods described herein, instead of or in addition to the Shh-I, a PDGFRα inhibitor is used, e.g., Crenolanib (CP-868596); Ki8751; Ponatinib (AP24534); Nintedanib (BIBF 1120); Dovitinib (TKI-258, CHIR-258); Masitinib (AB1010); Imatinib (STI571); Pazopanib; or KRN 633.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1. Association of vemurafenib resistance with ERK reactivation, AKT activation and PDGFRα upregulation in BRAF(V600E) melanoma cells.

Figure 4:
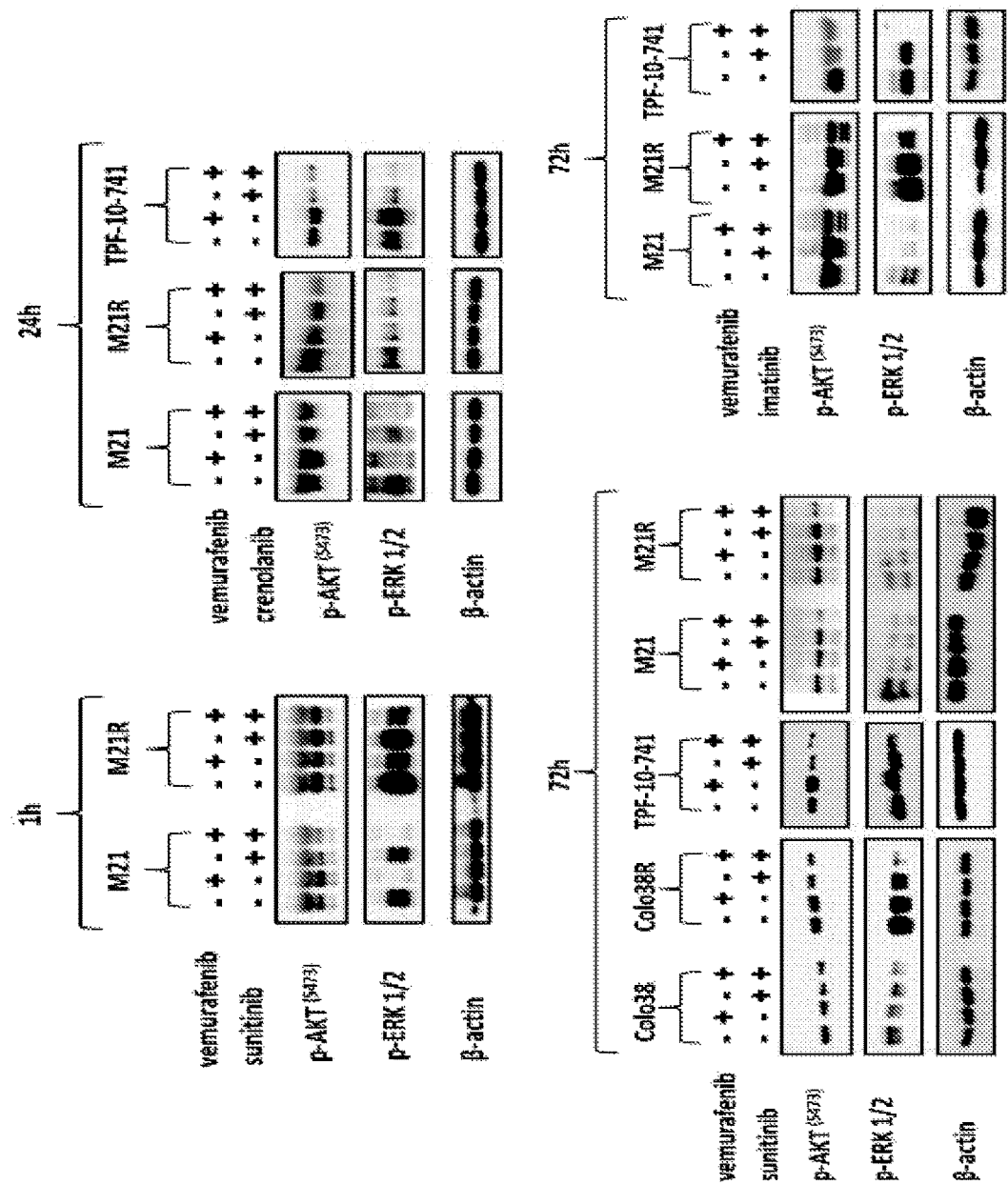

Colo38, Colo38R, M21, M21R and TPF-10-741 cells were treated with vemurafenib (1 µM). A. Following an incubation at indicated time points at 37° C. cells were harvested and lysed. Cell lysates were analyzed by western blot with the indicated mAbs. β-actin-was used as a loading control. B. Following a 48 h incubation at 37° C. cells were harvested and lysed. Cell lysates were analyzed by western blot with the indicated mAbs. β-actin or Calnexin were used as a loading control. The results presented are representative of the results obtained in three independent experiments.

FIG. 2. Restoration by PDGFRα downregulation of vemurafenib sensitivity of BRAF(V600E) melanoma cells with acquired BRAF-I resistance.

A. M21R and TPF-10-741 cells were transduced with PDGFRα-specific shRNA (#4) or with GFP-shRNA, used as a control, lentiviral particles. Transduced cells were treated with vemurafenib (1 µM). Following a three day incubation at 37° C. cells were harvested and lysed. Cell lysates were analyzed by western blot with the indicated mAbs. β-actin was used as a loading control. The results presented are representative of the results obtained in three independent experiments. B. PDGFRα-specific shRNA (#4) transduced M21R and TPF-10-741 cells were treated with the indicated vemurafenib concentrations. GFP-shRNA transduced M21R and TPF-10-741 cells were used as controls. Cell proliferation was determined by MTT assay following a three day incubation at 37° C. Percentage of cell proliferation was calculated as the ratio of treated cells to untreated GFP-shRNA transduced cells. Data are expressed as mean±SD of the results obtained in three independent experiments. *** indicates P<0.01.

FIG. 3. PDGFRα expression in melanoma tumors obtained from patients who acquired BRAF-I resistance.

Tumor biopsies of melanoma removed from patients were performed pre-treatment (day 0), at 10-14 days on treatment, and/or at the time of disease progression following treatment with BRAF-I or with BRAF-I and MEK-I. Frozen sections were fixed with 4% PFA and stained with H&E and PDGFRα-specific rabbit antibody. Scores were recorded semiquantitatively as 1+, 2+, 3+ and 4+, when, 1-25%, 26-50%, 51-75% and >75% of cells were stained, respectively. Patients were divided in two groups based on change of PDGFRα expression at IHC after treatment: those whose PDGFRα staining score had no or 1 point increase after treatment (≤1+) and those for whose PDGFRα staining score increased 2 or more points after treatment (>1+). A. Representative IHC staining and immunofluorescent staining of PDGFRα expression in melanoma patients before treatment, on treatment and at the time of disease progression in 5 out of 9 tumor biopsies. Magnification is indicated. B. Two groups of patients were graphed based upon RECIST criteria and compared as a percent of the total population of the PDGFRα stain score group. C. Two groups of patients were graphed based upon the time to disease progression utilizing Kaplan-Meier methods.

FIG. 4. Enhancement by PDGFRα inhibition of the signaling pathway inhibition by vemurafenib in melanoma cells harboring BRAF(V600E).

Enhancement by PDGFRα inhibition of the signaling pathway inhibition by vemurafenib in melanoma cells harboring BRAF(V600E). Colo38, Colo38R, M21, M21R and TPF-10-741 cells were treated with vemurafenib (1 µM) and/or sunitinib (3 µM) and/or imatinib (20 µM) and/or crenolanib (1 µM). Following an incubation at indicated time points at 37° C. cells were harvested and lysed. Cell lysates were analyzed by western blot with the indicated mAbs. β-actin was used as a loading control. The results presented are representative of the results obtained in three independent experiments.

FIG. 5. Enhancement by PDGFRα inhibition of the growth inhibition, signaling pathway inhibition and apoptosis induction by vemurafenib of BRAF(V600E) melanoma cells grafted in immunodeficient mice.

M21 and M21R cells were implanted subcutaneously in 20 SCID mice. When tumors became palpable, mice were randomly divided into 4 groups (5 mice/group). One group was treated with vemurafenib (12.5 mg/kg, twice daily), one with sunitinib (20 mg/kg, once each day) and one with the vemurafenib (12.5 mg/kg, twice daily) in combination with sunitinib (20 mg/kg, once each day). One group of mice was left untreated as a reference for the natural course of the disease. Efficacy data are plotted as mean tumor volume (in mm$^3$)±SD. The asterisk (*) indicates P<0.001(A, E). Tumors harvested from untreated and treated mice (three for each group) were lysed and analyzed for expression and activation of the indicated signaling pathways components. β-actin was used as a loading control (B, F). Tumor tissue sections were analyzed for the content of mitotic cells by staining with p-Histone H3 (Ser10) protein-specific antibodies. Mitotic tumor cells were quantified by counting 5 randomly selected high-power fields per section (magnification ×200) (C, G). Tumor tissue sections were analyzed for the content of apoptotic cells by staining with Cleaved Caspase-3 (Asp175)-specific antibodies. Apoptotic tumor cells were quantified by counting 5 randomly selected high-power fields per section (magnification ×200) (D, H). Data are presented as means±SD. * indicates P<0.001.

FIG. 6. Association of PDGFRα upregulation mediating vemurafenib resistance with Gli1 activation in melanoma cells harboring BRAF(V600E).

A. Colo38, Colo38R, M21, M21R and TPF-10-741 cells were treated with vemurafenib (1 µM). Following an incubation at indicated time points at 37° C. cells were harvested and lysed. Cell lysates were analyzed by western blot with the indicated mAbs. β-actin was used as a loading control. B. M21 and M21R cells were treated with vemurafenib (1 uM) and/or LDE225 (10 uM). Cell growth inhibition was determined by MTT assay following a three day incubation at 37° C. Percentage of cell growth inhibition was calculated as the ratio of treated to untreated cells. Data are expressed as the mean±SD of the results obtained in three independent experiments. The asterisk (*) indicates P<0.05. C. Colo38, Colo38R, M21 and M21R cells were treated with vemurafenib (1 µM) and/or LDE225 (10 uM). Following a 48 h incubation at 37° C. cells were harvested and lysed. Cell lysates were analyzed by western blot with the indicated mAbs. β-actin was used as a loading control. D. M21 cells were implanted subcutaneously in 20 SCID mice. When tumors became palpable, mice were randomly divided into 4 groups (5 mice/group). One group was treated with the BRAF-I vemurafenib (12.5 mg/kg/twice per day), one with LDE225 (40 mg/kg/day) and one with vemurafenib (12.5 mg/kg/twice per day) in combination with LDE225 (40 mg/kg/day). One group of mice was left untreated as a reference for the natural course of the disease. Efficacy data are plotted as mean tumor volume (in mm$^3$)±SD. The asterisks (***) indicate P<0.001.

Figure 7:
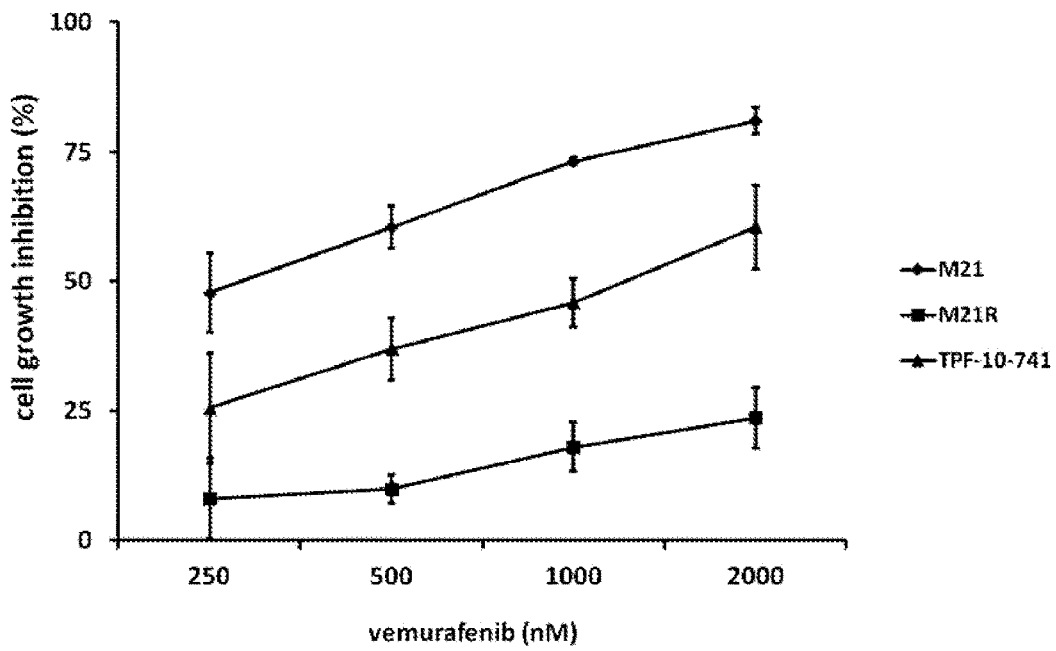

FIG. 7. BRAF(V600E) melanoma cell lines, autologous cells made resistant to BRAF-I by continuous exposure to increasing doses of vemurafenib and a melanoma cell line isolated from a patient who acquired BRAF-I resistance.

M21, M21R and TPF-10-741 cells were treated with the indicated concentrations of vemurafenib. Cell growth inhibition was determined by MTT assay following a five day incubation at 37° C. Percentage of cell growth inhibition was calculated as the ratio of treated to untreated cells at each vemurafenib dose. Data are expressed as the mean±SD of the results obtained in three independent experiments.

Figure 8:
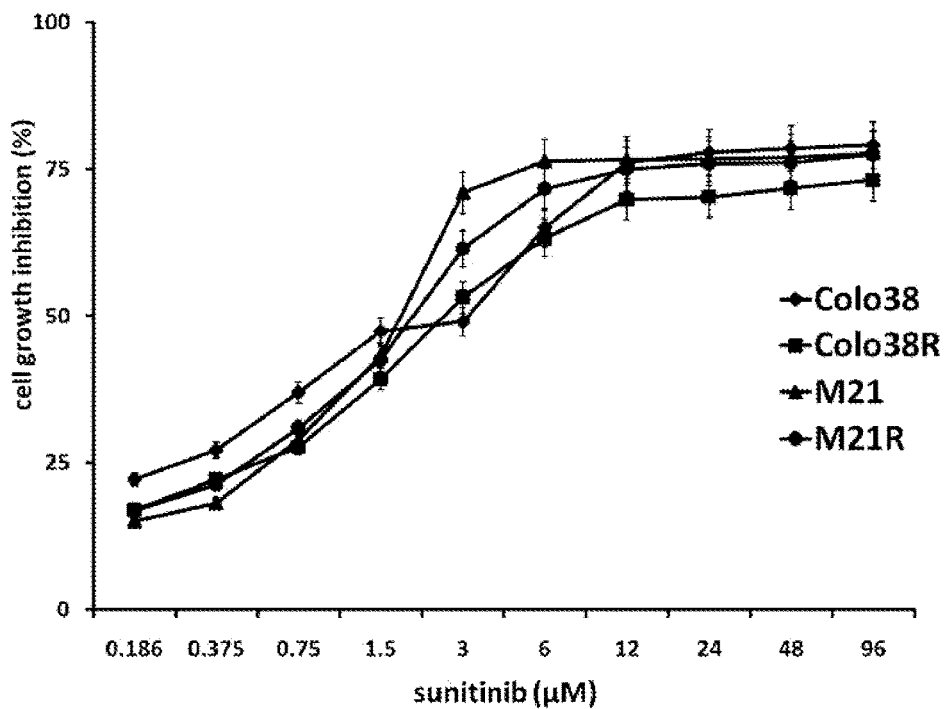

FIG. 8. Dose dependent effect of sunitinib on the in vitro proliferation of BRAF-I sensitive and resistant melanoma cells harboring BRAF(V600E).

Colo38, Colo38R, M21 and M21R cells were treated with the indicated concentrations of sunitinib. Cell growth inhibition was determined by MTT assay following a five day incubation at 37° C. Percentage of cell growth inhibition was calculated as the ratio of treated to untreated cells at each sunitinib dose. Data are expressed as mean±SD of the results obtained in three independent experiments.

Figure 9A:
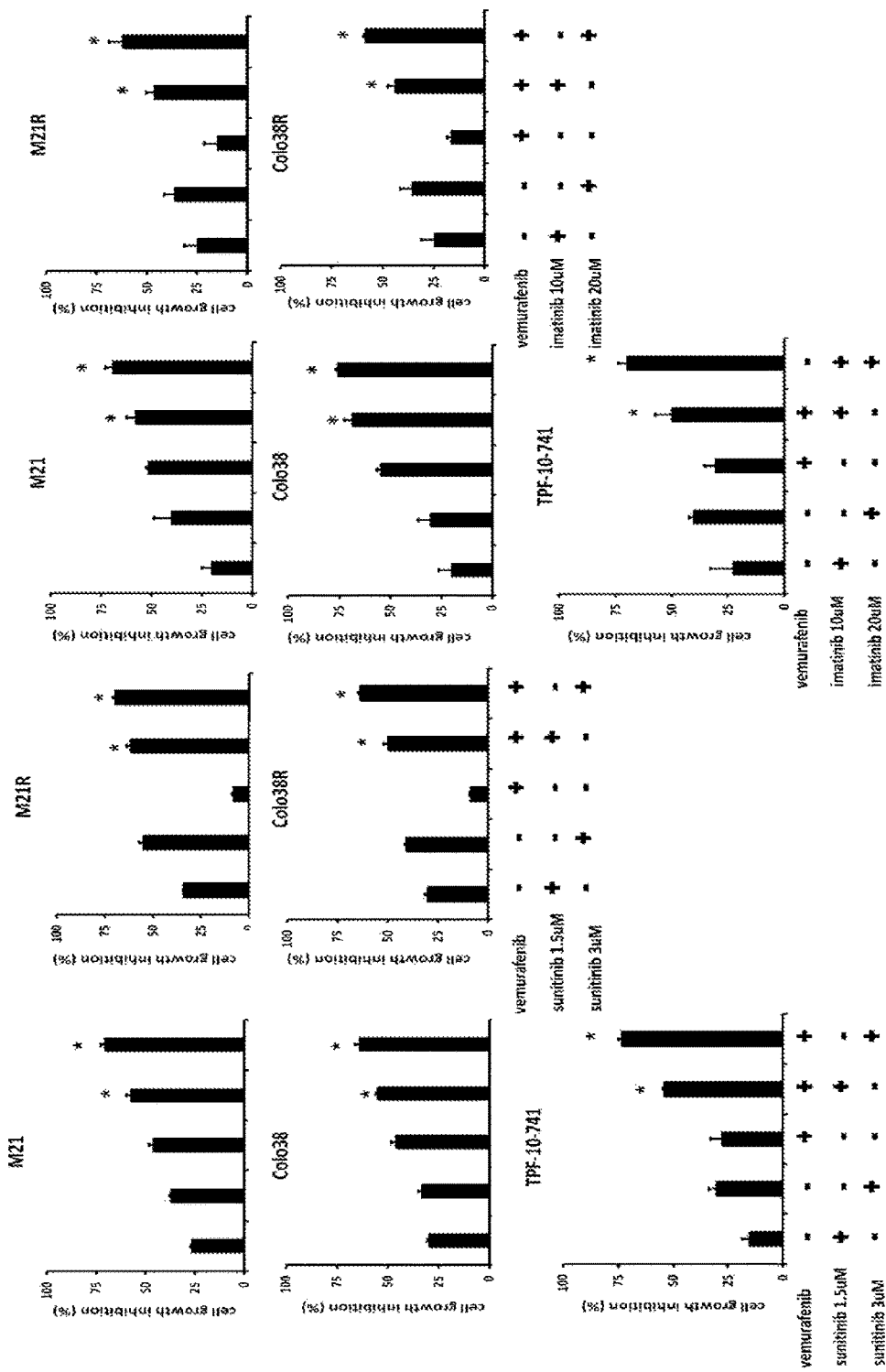
Figure 9B:
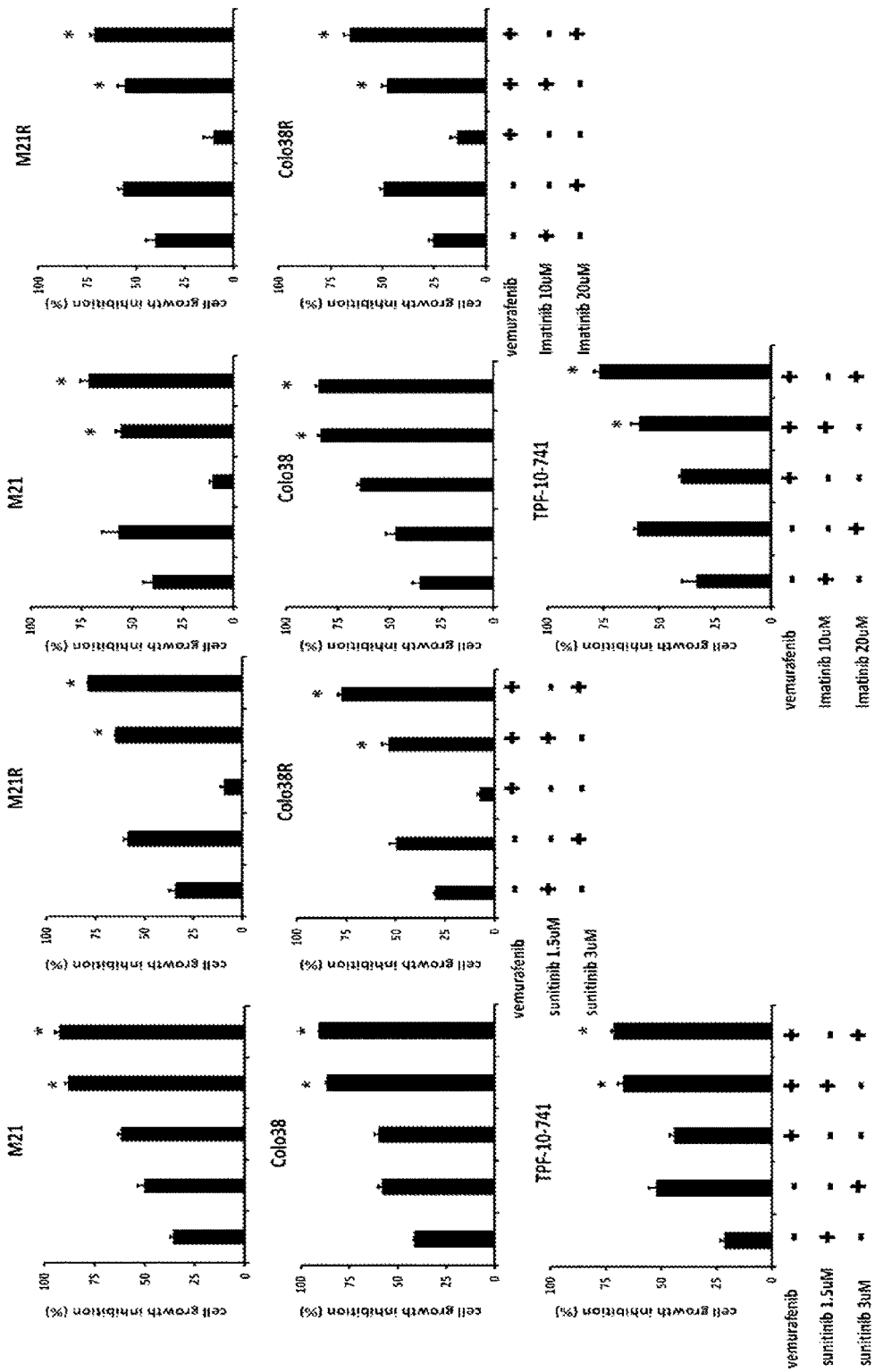

FIG. 9. Enhancement by PDGFRα inhibition with sunitinib or imatinib of the in vitro anti-proliferative activity of vemurafenib in BRAF-I sensitive and resistant melanoma cells harboring BRAF(V600E).

Colo38, Colo38R, M21, M21R and TPF-10-741 cells were treated with the indicated concentrations of vemurafenib and/or sunitinib or imatinib. Cell growth inhibition was determined by MTT assay following a three (A) and five (B) days of treatment. Percentage of cell growth inhibition was calculated as ratio of treated to untreated cells at each treatment. Data are expressed as mean±SD of the results obtained in three independent experiments. The asterisk (*) indicates P<0.05.

Figure 10A:
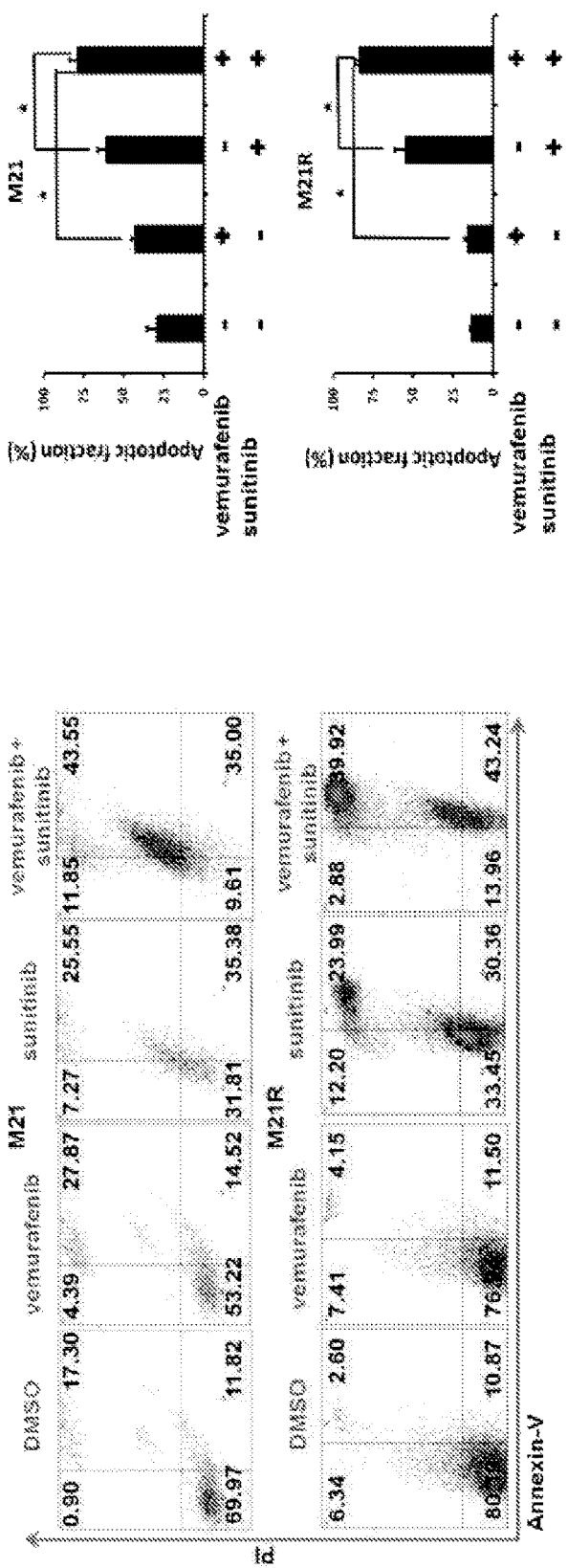

FIG. 10. Enhancement by PDGFRα inhibition of apoptosis induction by vemurafenib in melanoma cells harboring BRAF(V600E).

M21 and M21R cells (A), Colo38 and Colo38R cells (B), and TPF-10-741 cells (C) were treated with vemurafenib (500 nM) and/or sunitinib (3 µM). Following a 24 h incubation at 37° C. cells were harvested and stained with Annexin V and PI. The data presented are representative of the staining obtained in three independent experiments (left panel). The levels of apoptosis are plotted and expressed as mean fraction of apoptotic cells±SD of the results obtained in three independent experiments (right panel). The asterisk (*) indicates P<0.05.

Figure 11:
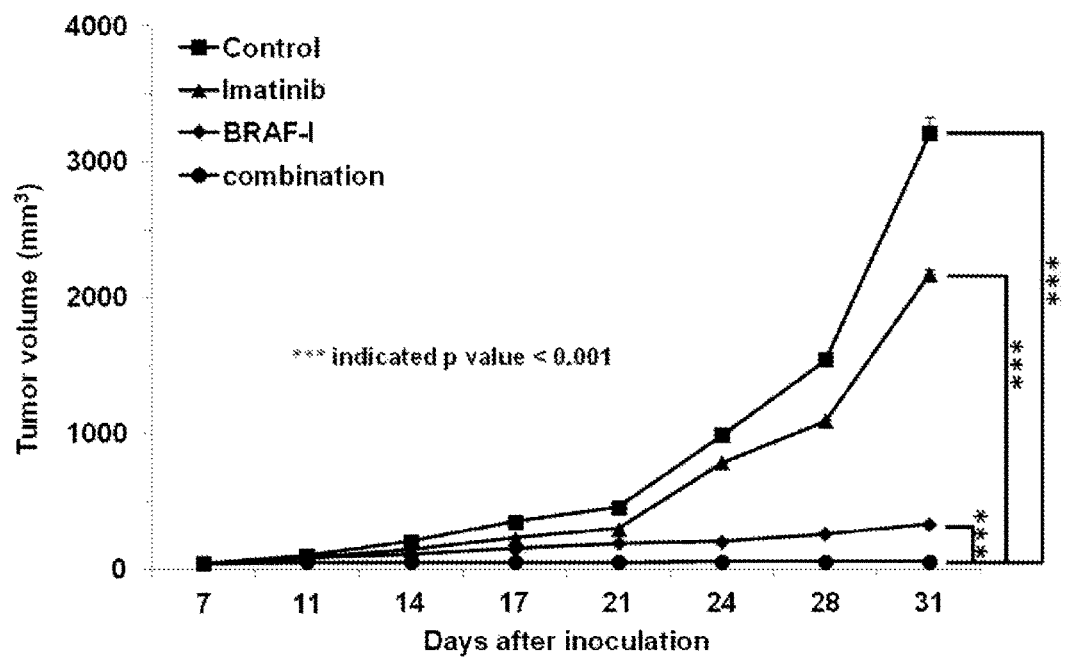

FIG. 11. Enhancement by PDGFRα inhibition of the growth inhibition by vemurafenib of BRAF(V600E) melanoma cells grafted in immunodeficient mice.

M21 cells were implanted subcutaneously in 20 SCID mice. When tumors became palpable, mice were randomly divided into 4 groups (5 mice/group). One group was treated with vemurafenib (25 mg/kg, twice daily), one with imatinib (100 mg/kg, daily) and one with the vemurafenib (25 mg/kg, twice daily) in combination with imatinib (100 mg/kg, daily). One group of mice was left untreated as a reference for the natural course of the disease. Efficacy data are plotted as mean tumor volume (in $mm^3$)±SD. The asterisk (***) indicates P<0.001.

Figure 12:
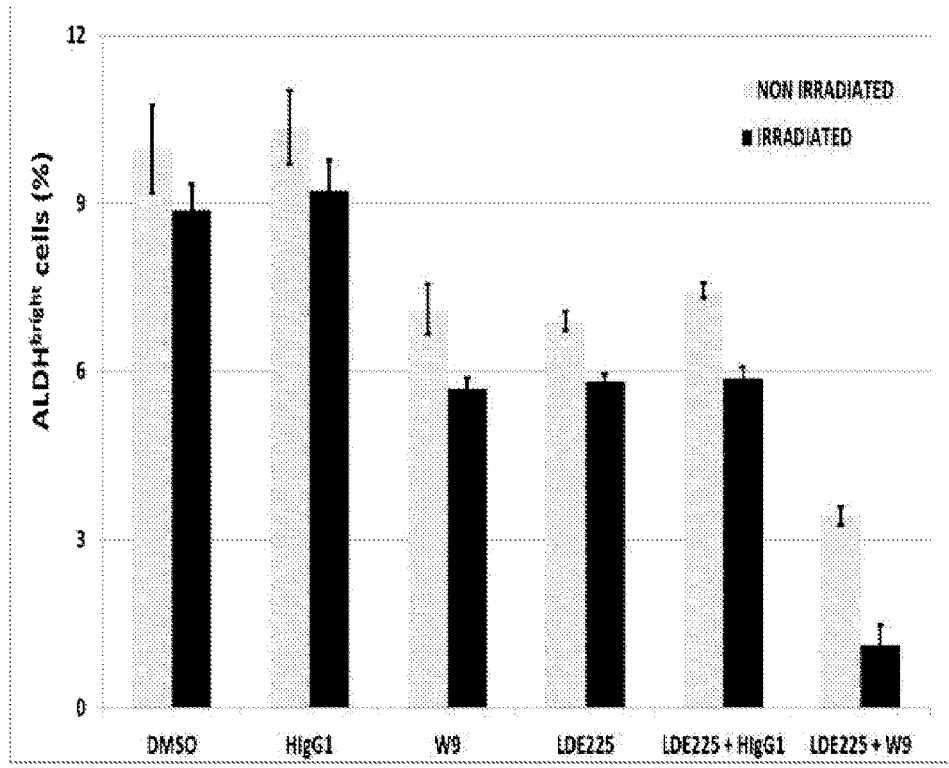

FIG. 12. Inhibition by mAb W9, radiation and LDE225 combination of human pancreatic CIC in vitro proliferation. Human PDAC2 cells ($4\times10^5$/ml) were irradiated at the dose of 20Gy and incubated with mAb W9 (20 µg/ml) and LDE225 (10 µM) for 72 hrs at 37° C. Cells were then stained with ALDEFLUOR with or without the DEAB inhibitor to identify ALDH$^{bright}$ cells. Non-irradiated cells and HIgG1 (20 µg/ml) treated cells were used as controls. The percentage of CICs identified as ALDH$^{bright}$ cells are plotted and expressed as mean±SD of the results obtained in three independent experiments. Treatment with mAb W9 is enhanced by radiation and LDE225. Furthermore mAb W9, LDE225 and 20Gy combination decrease CIC % to a significantly (P<0.01) greater extent than either of the single or double agents.

Figure 13:
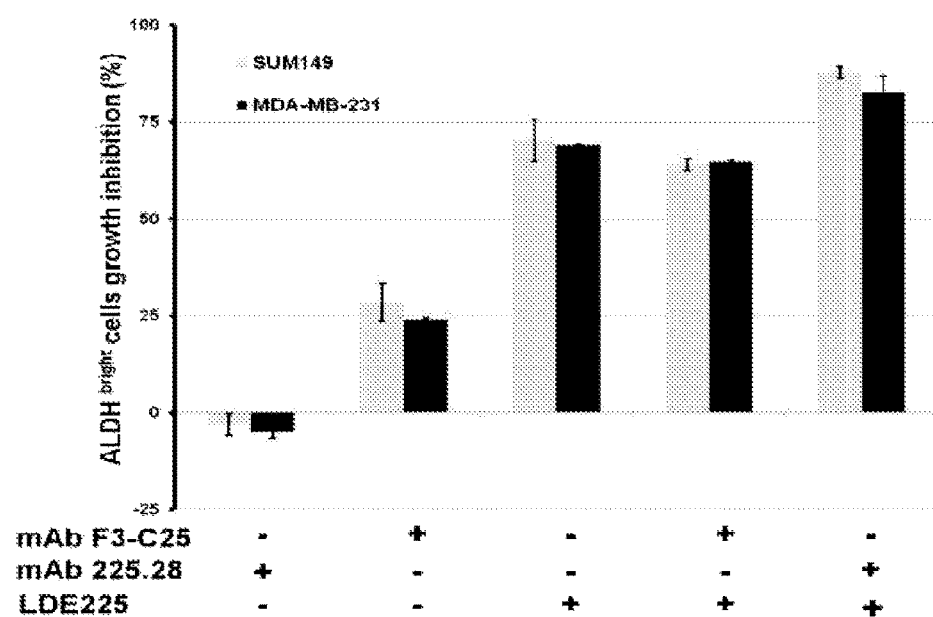

FIG. 13. Enhancement by CSPG4-specific mAb 225.28 of the CIC growth inhibition induced by LDE225, an inhibitor of the SHH pathway, in the TNBC cell line MDA-MB-231. MDA-MB-231 cells ($2.5\times10^5$/well) were starved for 6 hrs at 37° C., then incubated with mAb 225.28 (0.25 mg/ml) and LDE225 (10 uM) for 72 hrs at 37° C. in RPMI 1640 medium+1.5% FCS. The isotype matched mAb F3-C25 (0.25 mg/ml) was used as a control. Cells were stained with ALDEFLUOR with or without the DEAB inhibitor to identify ALDH$^{bright}$ cells. These results indicate that mAb 225.28 and LDE225 to suppress the growth of TNBC CICs as measured by the percentage of ALDH$^{bright}$ cells.

DETAILED DESCRIPTION

The methods described herein include combination therapies including administration of a sonic hedgehog inhibitor, plus one or more of radiation and a tumor antigen-specific monoclonal antibody (e.g., Grp94-specific mAb W9, or CSPG4-targeted mAbs), and/or a PDGFRα inhibitor.

Methods of Treatment

The methods described herein include methods for the treatment of cancer. In some embodiments, the disorder is melanoma or sarcoma. Generally, the methods include administering a therapeutically effective amount of a sonic hedgehog inhibitor, as described herein, plus one or more of radiation and a tumor antigen-specific monoclonal antibody (e.g., Grp94-specific mAb W9, or CSPG4-targeted mAbs), and/or a PDGFRα inhibitor, to a subject who is in need of, or who has been determined to be in need of, such treatment.

As used in this context, to "treat" means to ameliorate at least one symptom of the cancer. For example, administration of a therapeutically effective amount of a compound described herein for the treatment of a cancer will result in decreased tumor size, or reduced or delayed tumor growth rate.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Sonic Hedgehog (Shh) Pathway Inhibitors

A number of Shh inhibitors have been developed, including sulforaphane; vismodegib (GDC-0449; see Van Hoff et al., N Engl J Med 2009; 361:1164-72); TAK-441 (Ohashi et al., Bioorg Med Chem. 2012 Sep. 15; 20(18):5507-17); itraconazole; and erismodegib (also known as LDE225 or NVP-LDE225). The structure of erismodegib is as follows:

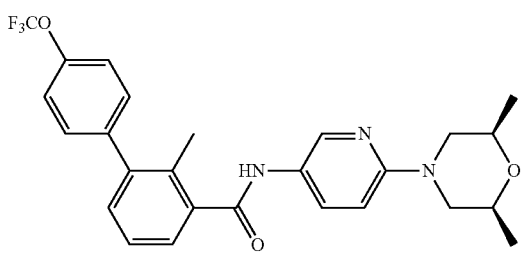 [SMILES: Cc1c(C(=O)Nc2ccc(N3C[C@@H](C)O[C@@H](C)C3)nc2)cccc1-c1ccc(OC(F)(F)F)cc1]

In some embodiments, the Shh pathway inhibitor binds to and inhibits the activity of Smoothened homologue (SMO). See, e.g., Romer and Curran, Cancer Res Jun. 15, 2005 65; 4975.

Antibodies Against Tumor-Specific Antigens

In some embodiments, the methods described herein include administering a combination of an Shh-I plus one or more antibodies directed against a tumor-specific antigen.

The term "antibody" as used herein refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, Antibodies: A Laboratory Manual (1988); Goding, Monoclonal Antibodies: Principles and Practice, (N.Y. Academic Press 1983); Howard and Kaser, Making and Using Antibodies: A Practical Handbook (CRC Press; 1st edition, Dec. 13, 2006); Kontermann and Dübel, Antibody Engineering Volume 1 (Springer Protocols) (Springer; 2nd ed., May 21, 2010); Lo, Antibody Engineering: Methods and Protocols (Methods in Molecular Biology) (Humana Press; Nov. 10, 2010); and Dübel, Handbook of Therapeutic Antibodies: Technologies, Emerging Developments and Approved Therapeutics, (Wiley-VCH; 1 edition Sep. 7, 2010).

Example of tumor antigens include Grp94 (e.g., targeted using mAb W9) and CSPG4 (e.g., targeted using CSPG4 specific-mAb 225.28).

Grp94 is a heat shock protein located in the endoplasmic reticulum of all mammalian cells. It is a chaperone essential for the conformational maturation of proteins, and regulates activation of several signaling pathways (e.g., tumor cell proliferation and survival). Like other members of the HSP90 family, the molecular chaperone Grp94 is required for the stability and activity of client proteins involved in the activation of signaling pathways associated with tumor cell survival and proliferation. Overexpression of Grp94 is associated with cellular transformation and tumorigenicity, and inhibition of Grp94 leads to depletion of oncogenic client proteins by the ubiquitin proteasome pathway. Specific inhibitors of Hsp90 have recently entered clinical trials, but application of Hsp90 inhibitors is experiencing some difficulties, especially because of their toxicity.

MAb W9 has unique specificity for an extracellular epitope of the heat shock protein (HSP) glucose regulated protein of 94000 daltons (Grp94). mAb W9 recognizes Grp94, since i) mass spectrometry analysis has identified two peptides unique of Grp94 in the approximately 100 KDa protein immunoprecipitated by mAb W9 from 5 human cancer cell lines; and ii) human melanoma cells transfected with Grp94 shRNA selectively lost their reactivity with mAb W9. Unlike other Grp94-specific mAbs described in the literature and/or available commercially, mAb W9 is able to selectively target malignant cells by recognizing a carbohydrate epitope which is expressed on malignant cells, but is not detectable on normal cells. See, e.g., US 2012/0148598 and US2012/0009194, both of which are incorporated by reference herein.

CSPG4 is expressed in patient derived Triple-negative breast cancer (TNBC) lesions. It is expressed at high levels not only on differentiated TNBC cells but also on TNBC cancer initiating cells (CICs). In TNBC cell lines CICs have been shown to express high level of Aldehyde Dehydrogenases A1 (ALDHbright; Ginestier et al., Cell Stem Cell. 2007; 1:555-567; Visus et al., Clinical cancer research: an official journal of the American Association for Cancer Research. 2011; 17:6174-6184) in addition to being able to form mammospheres in vitro and to be tumorigenic in SCID mice. In addition, CSPG4 is involved in signaling pathways associated with TNBC cell proliferation, survival and migration.

A number of antibodies against cancer-related antigens are known; exemplary antibodies are described in Ross et al., Am J Clin Pathol 119(4):472-485, 2003), as well as in Tables A-B, below.

TABLE A

| | Anticancer Antibodies | | | |
|---|---|---|---|---|
| Drug Name Generic (Brand) | Source (Partners) | Antibody Type | Target | Approved and Investigational Indications |
| Alemtuzumab (Campath) | BTG, West Conshohocken, PA (ILEX Oncology, Montville, NJ; Schering AG, Berlin, Germany) | Monoclonal antibody, humanized; anticancer, immunologic; multiple sclerosis treatment; immunosuppressant | CD52 | Chronic lymphocytic and chronic myelogenous leukemia; multiple sclerosis, chronic progressive |

TABLE A-continued

Anticancer Antibodies

| Drug Name Generic (Brand) | Source (Partners) | Antibody Type | Target | Approved and Investigational Indications |
|---|---|---|---|---|
| Daclizumab (Zenapax) | Protein Design Labs, Fremont, CA (Hoffmann-La Roche, Nutley, NJ) | Monoclonal IgG1 chimeric; immunosuppressant; antipsoriatic; antidiabetic; ophthalmologic; multiple sclerosis treatment | IL-2 receptor, CD25 | Transplant rejection, general and bone marrow; uveitis; multiple sclerosis, relapsing-remitting and chronic progressive; cancer, leukemia, general; psoriasis; diabetes mellitus, type 1; asthma; ulcerative colitis |
| Edrecolomab (Panorex) | GlaxoSmithKline, London, England | Monoclonal IgG2A murine; anticancer | Epithelial cell adhesion molecule | Cancer: colorectal |
| Gemtuzumab (Mylotarg) | Wyeth/AHP, Collegeville, PA | Monoclonal IgG4 humanized | CD33/cali-cheamicin | Acute myelogenous leukemia (patients older than 60 y) |
| Ibritumomab (Zevalin) | IDEC Pharmaceuticals | Monoclonal IgG1 murine; anticancer | CD20/ yttrium 90 | Low-grade lymphoma, follicular lymphoma, transformed non-Hodgkin lymphoma (relapsed or refractory) |
| Rituximab (Rituxan) | IDEC Pharmaceuticals, San Diego, CA (Genentech, South San Francisco, CA; Hoffmann-La Roche; Zenyaku Kogyo, Tokyo, Japan) | Monoclonal IgG1 chimeric; anticancer, immunologic; antiarthritic, immunologic; immunosuppressant | CD20 | Non-Hodgkin lymphoma, B-cell lymphoma, chronic lymphocytic leukemia; rheumatoid arthritis; thrombocytopenic purpura |
| Trastuzumab (Herceptin) | Genentech (Hoffmann-La Roche; ImmunoGen, Cambridge, MA) | Monoclonal IgG1 humanized; anticancer, immunologic | p185neu | Cancer: breast, non-small cell of the lung, pancreas |

TABLE B

Additional Anticancer Antibodies

| Drug Name Generic (Brand) | Source | Features | Investigational Indications |
|---|---|---|---|
| 2C4 antibody | Genentech | Chimeric monoclonal antibody; anticancer immunologic | Cancer: breast |
| ABX-EGF | Abgenix, Fremont, CA | Monoclonal antibody, human; anticancer immunologic | Cancer: renal, non-small cell of the lung, colorectal, prostate |
| ABX-MA1 | Abgenix | Humanized monoclonal antibody; anticancer immunologic | Melanoma |

TABLE B-continued

Additional Anticancer Antibodies

| Drug Name Generic (Brand) | Source | Features | Investigational Indications |
|---|---|---|---|
| ACA-125 | CellControl Biomedical, Martinsried, Germany | Monoclonal antibody; anticancer immunologic | Cancer: ovarian |
| Anti-HMI.24 | Chugai | Chimeric monoclonal antibody; anticancer immunologic | Myeloma |
| Anti-LCG MAbs | eXegenics, Dallas, TX | Monoclonal antibody; anticancer; imaging agent | Cancer: lung, general; diagnosis of cancer |
| Anti-PTHrP | Chugai | Chimeric monoclonal antibody; anticancer immunologic; osteoporosis | Hypercalcemia of malignancy; cancer, bone |
| Apolizumab | Protein Design Labs | Chimeric monoclonal antibody; anticancer immunologic | Non-Hodgkin lymphoma; chronic lymphocytic leukemia |
| AR54 | AltaRex | Murine monoclonal antibody; anticancer immunologic | Cancer: ovarian |
| Bevacizumab (Avastin) | Genentech, South San Francisco, CA | Anti-VEGF humanized monoclonal antibody; anticancer immunologic; antidiabetic; ophthalmologic | Cancer: colorectal, breast, non-small cell of the lung; diabetic retinopathy |
| BrevaRex MAb | AltaRex | Murine monoclonal antibody; anticancer immunologic | Cancer: myeloma, breast |
| CDP-860 | Celltech, Slough, England | Humanized monoclonal antibody; anticancer immunologic; cardiovascular | Cancer: general; restenosis |
| CeaVac | Titan Pharmaceuticals, South San Francisco, CA | Anti-CEA murine monoclonal antibody; anticancer immunologic vaccine | Cancer: colorectal, non-small cell of the lung, breast, liver |
| Cetuximab (C-225; Erbitux) | ImClone Systems | Anti-EGFR chimeric monoclonal antibody; anticancer immunologic | Cancer: head and neck, non-small cell of the lung, colorectal, breast, pancreas, prostate |
| Edrecolomab | Johnson & Johnson, New Brunswick, NJ | Murine monoclonal antibody; anticancer immunologic | Cancer: colorectal and breast |
| EMD 72 000 | Merck KGaA, Darmstadt, Germany | Chimeric monoclonal antibody; anticancer immunologic | Cancer: stomach, cervical, non-small cell of the lung, head and neck, ovarian |
| Epratuzumab (LymphoCide) | Immunomedics, Morris Plains, NJ | Chimeric monoclonal antibody; anticancer immunologic; immunosuppressant | Non-Hodgkin lymphoma |
| G-250, unconjugated | Johnson & Johnson | Chimeric monoclonal antibody; anticancer immunologic | Cancer: renal |
| GlioMAb-H | Viventia Biotech | Humanized monoclonal antibody; imaging agent; anticancer immunologic | Diagnosis of cancer; cancer, brain |
| H-11 scFv | Viventia Biotech, Toronto, Canada | Humanized monoclonal antibody; anticancer immunologic | Non-Hodgkin lymphoma, melanoma |

TABLE B-continued

Additional Anticancer Antibodies

| Drug Name Generic (Brand) | Source | Features | Investigational Indications |
|---|---|---|---|
| H22xKi-4 | Medarex | Chimeric monoclonal antibody; anticancer immunologic | Hodgkin lymphoma |
| huJ591 MAb, BZL | Millennium Pharmaceuticals, Cambridge, MA; BZL Biologics, Framingham, MA | Chimeric monoclonal antibody; anticancer immunologic | Cancer: prostate and general |
| IGN-101 | Igeneon, Vienna, Austria | Murine monoclonal antibody; anticancer immunologic | Cancer: non-small cell of the lung, liver, colorectal, esophageal, stomach |
| IMC-1C11 | ImClone Systems | Chimeric monoclonal antibody; anticancer immunologic | Cancer: colorectal |
| Imuteran | Nonindustrial source | Monoclonal antibody; anticancer immunologic | Cancer: breast, ovarian |
| ING-1 | Xoma, Berkeley, CA | Chimeric monoclonal antibody; anticancer immunologic | Cancer: breast, lung (general), ovarian, prostate |
| ior-t1 | Center of Molecular Immunology, Havana, Cuba | Murine monoclonal antibody; anticancer immunologic; antipsoriatic; antiarthritic immunologic | T-cell lymphoma; psoriasis; rheumatoid arthritis |
| KSB-303 | KS Biomedix, Guildford, England | Chimeric monoclonal antibody; anticancer immunologic | Diagnosis of cancer; cancer, colorectal |
| KW-2871 | Kyowa Hakko, Tokyo, Japan | Chimeric monoclonal antibody; anticancer immunologic | Melanoma |
| Labetuzumab | Immunomedics | Chimeric monoclonal antibody; immunoconjugate; anticancer immunologic | Cancer: colorectal, breast, small cell of the lung, ovarian, pancreas, thyroid, liver |
| Lintuzumab (Zamyl) | Protein Design Labs, Fremont, CA | Chimeric monoclonal antibody; anticancer immunologic | Acute myelogenous leukemia; myelodysplastic syndrome |
| MAb, AME | Applied Molecular Evolution, San Diego, CA | Chimeric monoclonal antibody; anticancer immunologic; imaging agent; antiarthritic immunologic; ophthalmologic; cardiovascular | Cancer: sarcoma, colorectal; rheumatoid arthritis; psoriatic arthritis |
| MDX-010 | Medarex | Humanized anti-HER-2 monoclonal antibody; anticancer immunologic; immunostimulant | Cancer: prostate, melanoma; infection, general |
| MDX-210 | Medarex, Princeton, NJ; Immuno-Designed Molecules, Havana, Cuba | Bispecific chimeric monoclonal antibody; anti-HER-2/neu-anti-Fc gamma RI; anticancer immunologic | Cancer: ovarian, prostate, colorectal, renal, breast |
| MDX-220 | Immuno-Designed Molecules | Chimeric monoclonal antibody; anticancer immunologic | Cancer: prostate, colorectal |
| Mitumomab | ImClone Systems, New York, NY | Murine monoclonal antibody; anticancer immunologic | Small cell cancer of the lung; melanoma |

TABLE B-continued

Additional Anticancer Antibodies

| Drug Name Generic (Brand) | Source | Features | Investigational Indications |
| --- | --- | --- | --- |
| Monopharm-C | Viventia Biotech | Monoclonal antibody; anticancer immunologic; imaging agent | Cancer: colorectal; diagnosis of cancer |
| MRA | Chugai Pharmaceutical, Tokyo, Japan | Chimeric monoclonal antibody; antiarthritic immunologic; anticancer immunologic; GI inflammatory and bowel disorders | Rheumatoid arthritis; cancer, myeloma; Crohn disease; Castleman disease |
| MT-103 | Micromet | Murine monoclonal antibody; anticancer immunologic | B-cell lymphoma, non-Hodgkin lymphoma, chronic myelogenous leukemia, acute myelogenous leukemia |
| MT-201 | Micromet, Munich, Germany | Humanized monoclonal antibody; anticancer immunologic | Cancer: prostate, colorectal, stomach, non-small cell of the lung |
| Onyvax-105 | Onyvax, London, England | Monoclonal antibody; anticancer immunologic | Cancer: colorectal; sarcoma, general |
| Oregovomab | AltaRex, Waltham, MA | Monoclonal antibody, murine; anticancer immunologic; immunoconjugate | Cancer: ovarian |
| Prostate cancer antibody | Biovation, Aberdeen, Scotland | Monoclonal antibody; anticancer | Cancer: prostate |
| R3 | Center of Molecular Immunology | Chimeric monoclonal antibody; anticancer immunologic; imaging agent; immunoconjugate | Cancer: head and neck; diagnosis of cancer |
| SGN-30 | Seattle Genetics, Seattle, WA | Monoclonal antibody; anticancer immunologic; multiple sclerosis treatment; immunosuppressant; immunoconjugate | Hodgkin lymphoma |
| Therex | Antisoma, London, England | Chimeric monoclonal antibody; anticancer immunologic | Cancer: breast |
| Tositumomab (Bexxar) | Corixa, Seattle, WA | Anti-CD20 murine monoclonal antibody with iodine 131 conjugation | Non-Hodgkin lymphoma |
| TRAIL-RI MAb, CAT | Cambridge Antibody Technology, Cambridge, England | Humanized monoclonal antibody; anticancer immunologic | Cancer: general |
| TriAb | Titan Pharmaceuticals | Murine monoclonal antibody; anticancer immunologic | Cancer: breast, non-small cell of the lung, colorectal |
| TriGem | Titan Pharmaceuticals | Murine monoclonal antibody; anticancer immunologic | Cancer: melanoma, small cell of the lung, brain |
| Visilizumab | Protein Design Labs | Chimeric monoclonal antibody; immunosuppressant; anticancer immunologic; GI inflammatory and bowel disorders | Transplant rejection, bone marrow; cancer, T-cell lymphoma; ulcerative colitis; myelodysplastic syndrome; systemic lupus erythematosus |

BRAF Inbibitors

A number of BRAF inhibitors are known in the art, including Vemurafenib, GDC-0879, PLX-4720, GSK2118436, Sorafenib Tosylate. dabrafenib, and LGX818.

PDGFRα Inhibitors

A number of PDGFRα inhibitors are known in the art, including Crenolanib (CP-868596); Ki8751; Ponatinib (AP24534); Nintedanib (BIBF 1120); Dovitinib (TKI-258, CHIR-258); Masitinib (AB1010); Imatinib (STI571); Pazopanib; and KRN 633. PDGFRα inhibitors can be used in any of the methods described herein, e.g., instead of or in addition to a Shh-I.

Treating BRAF-Inhibitor Resistant Cancers

In over 50% of metastatic melanoma patients their melanoma harbors the BRAF(V600E) point mutation (T1799A) [1,2]. Mutant BRAF(V600E) represents a constitutively active protein serine kinase that leads to the sustained activation of the BRAF→MEK1/2→ERK1/2 MAP kinase pathway[3,4]. This pathway plays a critical role in the regulation of gene expression, cell proliferation and survival, which contributes to the initiation and progression of melanoma[5,6]. Clinical trials have demonstrated that the BRAF inhibitor (BRAF-I) PLX4032 (vemurafenib) and other inhibitors in its class (GSK2118436 or dabrafenib) can induce tumor regression in >50% of patients with metastatic melanoma harboring the BRAF(V600E) mutation and improve both progression-free and overall survival[7,8]. Although the clinical activity of BRAF-I therapy is a major breakthrough in the treatment of metastatic melanoma, the median time to disease progression is less than 7 months, due to acquired resistance[8]. Furthermore complete responses to vemurafenib are only observed in 5% of patients, as a consequence of intrinsic BRAF-I resistance[7,9].

The multiple mechanisms underlying melanoma BRAF-I resistance can be classified into two groups. The first includes ERK signaling reactivation, due to a point mutation in MEK1[10,11], amplification of mutant BRAF(V600E)[12], elevated CRAF activity[13], activating NRAS mutation[14], increased levels of COT/Tp12[15] and/or aberrantly spliced BRAF(V600E)[16]. The second category includes activation of alternative pro-tumorigenic pathways due to an increase in receptor tyrosine kinase (RTK) driven signaling, via platelet-derived growth factor receptor β (PDGFRβ) overexpression[14,17], insulin-like growth factor 1 receptor (IGF1R) activation[18], phosphatase and tensin homolog (PTEN) loss and activation of PI3K/AKT[19]. Most of these mechanisms have corroborating clinical evidence[10,14-16,18] which has led to therapeutic strategies combining BRAF-I with other treatment modalities such as the concurrent administration of BRAF-I and MEK inhibitors (MEK-I)[20].

Unfortunately, the mechanisms described to date account for the cause of resistance in less than 50% of patients whose disease relapses while being treated with a BRAF-I. Therefore, identification and characterization of unknown pathways mediating BRAF-I resistance are essential for the rational design of targeted strategies to prevent and overcome BRAF-I resistance across this entire population of patients.

In this study we demonstrate that both melanoma cell lines with acquired BRAF-I resistance and lesions harvested from patients who acquire vemurafenib resistance develop PDGFRα upregulation implying its contribution in BRAF-I resistance. Furthermore, we demonstrate that the PDGFRα mediated BRAF-I resistance can be overcome by combining vemurafenib with a PDGFRα inhibitor (PDGFRα-I) such as sunitinib[21], imatinib[22], or crenolanib (Dai et al., Clin Cancer Res. 2013 Dec. 15; 19(24):6935-42) both in vitro and in vivo. Lastly, we show that activation of the Sonic Hedgehog Homolog pathway (SHH) is a mechanism by which PDGFRα upregulation mediates intrinsic and acquired BRAF-I resistance in melanoma, and that combination therapy with a BRAF-I and a SHH inhibitor (SHH-I) can overcome resistance to BRAF-I monotherapy in vitro and in vivo.

PDGFRα is also overexpressed in sarcoma and glioma. It is involved in tumor growth, metastasis and neoangiogenesis, as well as in the development of resistance to cytotoxic therapy[28]. These functional properties of PDGFRα are likely to reflect its ability to engage signaling pathways, such as RAS/RAF/MEK/ERK and PI3K/AKT which play a role in tumor cell proliferation and aggressive tumor phenotypes. The present study demonstrates that PDGFRα is expressed by human melanoma cells both in vitro and in vivo. Its upregulation in human melanoma cells harboring the BRAF (V600E) mutation is shown for the first time to be associated with the loss of their sensitivity to the anti-proliferative and pro-apoptotic activity of the BRAF-I vemurafenib both in vitro and in vivo. The association between PDGFRα upregulation and vemurafenib resistance reflects a cause-effect relationship, since sensitivity to vemurafenib is restored in melanoma cells which downregulate PDGFRα expression following transduction with a PDGFRα-specific shRNA. An association between the PDGFRα and BRAF (V600E) mutation is also observed in wild type PDGFRα gastrointestinal stromal tumors which acquire the BRAF (V600E) mutation when they develop resistance to PDGFRα-I[29-32].

Vemurafenib resistance of melanoma cells harboring a BRAF mutation reflects ERK and AKT activation induced by PDGFRα upregulation, since inhibition of its synthesis by PDGFRα-specific shRNA causes a reduction of ERK and AKT activation and restores sensitivity to BRAF-I. A similar effect has been demonstrated for HGF/c-met mediated resistance to BRAF-I[33]. This is corroborated by the in vitro and in vivo results obtained by inhibiting the function of PDGFRα with the tyrosine kinase inhibitor sunitinib, imatinib or crenolanib. Vemurafenib in combination with a PDGFRα-I inhibits in vitro proliferation and induces apoptosis of melanoma cells with a PDGFRα upregulation mediated BRAF-I resistance. These results are paralleled by our in vivo findings. Vemurafenib in combination with the PDGFRα-I inhibited the growth and induced apoptosis in human melanoma cells with PDGFRα upregulation mediated BRAF-I resistance engrafted in immunodeficient mice. These effects are mediated by the inhibition of the RAF/MEK/ERK and PI3K/AKT signaling pathways since the levels of p-ERK and p-AKT were markedly reduced in melanoma cells with PDGFRα upregulation mediated BRAF-I resistance following in vitro or in vivo treatment with vemurafenib in combination with a PDGFRα-I. It is noteworthy that vemurafenib in combination with a PDGFRα-I has a significantly greater anti-proliferative and pro-apoptotic effect than either agent alone both in vitro and in vivo also with BRAF-I sensitive human melanoma cells which expresses PDGFRα. Therefore our results suggest that the combinatorial strategy we have developed may overcome not only the acquired, but also the intrinsic BRAF-I resistance if PDGFRα is expressed. Furthermore they confirm that simultaneous inhibition of both the AKT and ERK pathways is more effective in suppressing tumor cell proliferation and in inducing apoptosis in both BRAF-I sensitive and resistant melanoma cells[18,34-40].

PDGFRα upregulation has been found to be regulated by the SHH pathway and by Gli1 activation[23-26]. Our data confirm this association since treatment with BRAF-I as well as for PDGFRα expression induces a Gli1 upregulation. The latter results are associated with PDGFRα upregulation which leads to BRAF-I resistance since treatment with a SHH-I, which inhibits Gli1 activation, downregulates the expression of PDGFRα. Furthermore PDGFRα downregulation by the SHH-I in combination with vemurafenib enhances tumor growth inhibition and decreases ERK and AKT activation in both sensitive and resistant cell lines.

PDGFRα is not the only growth factor receptor which plays a role in BRAF-I resistance. IGFR1[18] and PDGFRβ[14,17] are involved in the acquired BRAF-I resistance of melanoma. BRAF-I resistance mediated by IGFR and PDGFRβ, similar to PDGFRα, is mediated by ERK and AKT activation. However as reported[17] and as found by us the PDGFRα/PDGFRβ inhibitors sunitinib and imatinib are not able to overcome BRAF-I resistance mediated by PDGFRβ upregulation. The latter finding reflects the lack of inhibition of ERK activation in spite of the inhibition of AKT activation since the inhibition of these two downstream components of the RAF/MEK/ERK and PI3K/AKT signaling pathways by a PDGFRβ-specific shRNA restored sensitivity of melanoma cells to vemurafenib.

The clinical relevance of our results is suggested by two lines of evidence. First, PDGFRα expression was upregulated in 5 out of the 9 melanoma lesions with a BRAF (V600E) mutation surgically removed from patients who had developed BRAF-I resistance. Second, the extent of PDGFRα increase in melanoma lesions, as indicated by the IHC staining intensity, was associated with the clinical course of the disease. Specifically a marked increase in PDGFRα was found to be associated with a shorter time to progression and less tumor regression based on RECIST criteria. Notably, baseline expression of PDGFRα did not correlate with response or time to progression. In order to utilize the phenomenon we have observed as a method for patient selection, one would need to monitor PDGFRα upregulation in tumor biopsy specimens or develop a non-invasive or surrogate method to detect upregulation.

These findings have important translational implications, potentially effective in counteracting the BRAF-I Gli1/PDGFRα-mediated resistance of melanoma. The translation of this approach into the clinic is facilitated by the availability of FDA approved drugs to use in combination. Furthermore these data suggest that PDGFRα may be a biomarker for patients with BRAF-mutant melanoma, predicting who will or will not respond to BRAF-I or combination BRAF-I and MEK-I. The finding of upregulated PDGFRα has therapeutic implications, as these patients may potentially benefit from treatment with BRAF-I in combination with PDGFRα-I or SHH-I.

Resistance to BRAF inhibitors is a major obstacle to the clinical success of melanoma treatment. Several mechanisms of BRAF inhibitor resistance have been identified. The data presented herein demonstrate for the first time that a broad range of the described mechanisms can be driven by upregulation and/or activation of sonic hedgehog pathway. These resistances can be overcome by combining a sonic hedgehog inhibitor and a BRAF inhibitor.

Thus the present methods for treating BRAF inhibitor (BRAF-I)-resistant cancers, e.g., melanoma, carcinoma, e.g., colon cancer, thyroid cancer, pancreatic adenocarcinoma, triple negative breast cancer, glioma, or sarcoma, include the administration of therapeutically effective amounts of at least one BRAF-I plus at least one Shh-I.

Combination Therapy with Sonic Hedgehog Pathways Inhibitors and Tumor Antigen-Specific Monoclonal Antibody-Based Immunotherapy The recurrence of disease in patients with solid tumors treated with Tumor Antigen-specific monoclonal antibodies in combination with chemo- and/or radio-therapy may reflect the persistence of Cancer initiating cells because according to the cancer stem cell theory these cells are responsible for disease recurrence and metastatic spread. To overcome these limitations we have developed a combinatorial strategy that includes administration of tumor antigen-specific monoclonal antibodies with inhibitor of signaling pathways activated in Cancer initiating cells such as inhibitors of the Sonic Hedgehog pathways in triple negative breast cancer and in pancreatic ductal cancer. We show for the first time that this combinatorial strategy completely eradicates in vitro the so called cancer initiating cells. These effects are mediated by an enhanced apoptosis and inhibition of signaling pathways associated with proliferation and survival of cancer cells including cancer initiating cells.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

EXAMPLES

The invention is further described in the following examples, which do not limit the scope of the invention described in the claims.

Material and Methods

The following materials and Methods were used in Example 1, below.

Cell Cultures

The parental BRAF(V600E) melanoma cell lines Colo38 and M21 were cultured in RPMI 1640 medium (Mediatech, Inc. Herndon, Va.) supplemented with 2 mmol/L L-glutamine (Mediatech) and 10% fetal calf serum (FCS; Atlanta Biologicals, Lawrenceville, Ga.). The BRAF(V600E) melanoma cell line TPF-10-741 was cultured in DMEM (Mediatech) supplemented with 2 mmol/L L-glutamine and 10% FCS. This cell line was started from a cutaneous metastasis of the melanoma patient TPF-10-741who had developed BRAF-I resistance following treatment with vemurafenib. Melanoma cell lines with acquired vemurafenib resistance (Colo38R and M21R) were generated by propagating parental Colo38 and M21 cells in increasing concentrations of BRAF-I (up to 2 µM) to achieve chronic selection. Colo38R and M21R were cultured in RPMI 1640 medium supplemented with 2 mmol/L L-glutamine, 10% FCS and 500 nM vemurafenib. All cells were cultured at 37° C. in a 5% $CO_2$ atmosphere.

Chemical Reagents, Antibodies and shRNAs

Vemurafenib and LDE225 were purchased from ChemieTek (Indianapolis, Ind.). Sunitinib, imatinib and crenolanib were purchased from Selleck Chemicals LLC (Houston, Tex.). 3-(4,5-Dimethylthiazol-2yl)-2,5-diphenyl tetrazolium bromide (MTT) was purchased from Sigma (St. Louis, Mo.). Phospho (p)-AKT (Ser473)-, AKT-, p-PI3K p85 (γ458)-, p-CRAF (S289/296/301)-, p-MEK 1/2 (S217/221)-, p-ERK 1/2 (Thr202/Tyr204)-, ERK1/2-, PDFGRβ-, p-PDGFRα-, PDGFRα-, PTEN-, VEGFR2-, Cleaved Caspase-3 (Asp175)-, p-Histone H3 (Ser10)-, Gli1- and β-actin-specific monoclonal antibodies (mAbs) were purchased from Cell Signaling Technology (Danvers, Mass.). The calnexin-specific mAb TO-5 was developed and characterized as described[1]. PDGFRα-specific short hairpin RNA (shRNA) and GFP-shRNA were provided by the Vector Core Facility of the University of Pittsburgh Cancer Institute (Pittsburgh, Pa.).

Cell Proliferation and MTT Assay

Cells were plated in triplicate in 96-well microtiter plates at the density of $2.5 \times 10^3$ per well in 100 ul in RPMI 1640 or DMEM medium supplemented with 2% FCS and treated with vemurafenib and/or PDGFRα-I (sunitinib or imatinib or crenolanib) and/or SHH-I LDE225. DMSO (vehicle of the drugs) concentration was maintained at 0.02% in all wells. Cell proliferation was evaluated by MTT assay at indicated time points. MTT assay was carried out as reported elsewhere[2]. Data were expressed as percent of inhibition or percent of proliferation of treated cells compared with the untreated control cells. All experiments were performed three independent times in triplicates.

Western Blot Analysis

For samples preparation from cell lines, cells were seeded at the density of $1 \times 10^5$ perwell in a 6-well plate in medium supplemented with 2% FCS and treated with vemurafenib (1 µM), sunitinib (3 µM), imatinib (20 µM), crenolanib (1 uM), LDE225 (10 µM), vemurafenib 10 plus sunitinib or imatinib, and vemurafenib plus LDE225 at 37° C. in a 5% CO2 atmosphere for the indicated time points. The DMSO (vehicle of the drugs) concentration was maintained at 0.02% in all wells. Untreated cells were used as a control. Cells were collected and lysed in lysis buffer [10 mM Tris-HCl (pH 8.2), 1% NP40, 1 mM EDTA, 0.1% BSA, 150 mM NaCl) containing 1/50 (vol/vol) of protease inhibitor cocktail (Calbiochem, La Jolla, Calif.). For sample preparation from tumor xenografts, tumors were extracted at the time of killing, harvested and stored at −80° C. Proteins were extracted by homogenization in the presence of 2 to 5 ml lysis buffer. Western blot assay for signaling-related proteins was carried out as described[3]. The investigator who analyzed the sample from tumor xenografts was blinded to the type of treatment received by the mice used as the source of the tumor.

Transduction of Melanoma Cells with Lentiviral Vectors Encoding shRNA

Colo38R, M21R and TPF-10-741 cells were seeded at the density of $6 \times 10^4$ per well in a 6-well plate and incubated in culture medium for 24 h at 37° C. in a 5% $CO_2$ atmosphere prior to viral infection. Cells were transduced with PDGFRα-specific shRNAs [Target sequence: CCAGCCTCATATAAGAAGAAA (#1; SEQ ID NO:1), CCAGCTTTCATTACCCTCTAT (#2; SEQ ID NO:2), CGGTGAAAGACAGTGGAGAT (#3; SEQ ID NO:3), CCCAACTTTCTTATCCAACTT (#4; SEQ ID NO:4), CAATGGACTTACCCTGGAGAA (#5; SEQ ID NO:5)] or GFP-shRNA, used as a control, lentiviral particles ($1 \times 10^6$ per well) in presence of polybrene (2 µg/ml) as described elsewhere[4]. Following an 18 h incubation at 37° C., culture medium was removed and replaced with fresh culture medium. Following an additional incubation for up to 72 h at 37° C., cells were analyzed for GFP expression under the microscope, split, enriched for infected cells by selection with puromycin (2.5 ug/ml) and collected for further analysis.

Flow Cytometry

These assays were carried out as described elsewhere[5]. In briefly cells were seeded in 6-well plates in triplicate at the density of $1 \times 10^5$ per well and treated with vemurafenib and/or sunitinib. Following a 24 h treatment apoptotic cells were identified by staining with Annexin-V and PI (BD Bioscience, San Jose, Calif.) for 15 min at room temperature. Flow cytometry data were analyzed using Summit v4.3 software (DAKO, Carpinteria, Calif.).

In Vivo Studies

C.B-17 severe combined immunodeficient (SCID) female mice (8-10 week old) were purchased from Taconic Farms, Inc. (Hudson, N.Y.). Parental and BRAF-I resistant cell lines M21 and M21R ($1 \times 10^6$ cells/mouse) were implanted subcutaneously in the right lateral flank of mice. A total of 20 SCID mice was challenged with each cell line. Body weight and tumor volume were measured twice per week. Tumor volume was measured by vernier caliper. Treatment was initiated 10 days after cell inoculation when the tumor developed and had a diameter of around 0.4 cm. Mice were randomly divided into 4 groups of 5 mice each. Mice in Group 1 were treated with vemurafenib (12.5 mg/kg/twice per day[6]), those in Group 2 with sunitinib (20 mg/kg/day)[7] and those in Group 3 with vemurafenib (12.5 mg/kg/twice per day) plus sunitinib (20 mg/kg/day). Mice in Group 4 were left untreated as a reference for the natural course of the disease.

For mice treated with vemurafenib and imatinib combination mice were randomly divided into 4 groups of 5 mice each. Mice in Group 1 were treated with vemurafenib (25 mg/kg/twice per day[6]), those in Group 2 with imatinib (100 mg/kg/day)[8] and those in Group 3 with vemurafenib (25 mg/kg/twice per day) plus imatinib (100 mg/kg/day). Mice in Group 4 were left untreated as a reference for the natural course of the disease.

To test vemurafenib and LD225 combination, mice were randomly divided into 4 groups of 5 mice each. Mice in Group 1 were treated with vemurafenib (12.5 mg/kg/twice per day), those in Group 2 with LDE225 (40 mg/Kg/day) (Fendrich et al., Annals of Surgery. 2011; 254(5):818-823; discussion 823), and those in Group 3 with vemurafenib (12.5 mg/kg/twice per day) plus LDE225 (40 mg/kg/day). Mice in Group 4 were left untreated as a reference for the natural course of the disease.

Drugs were administered by oral gavage. When tumor diameter from untreated mice reached 2.0 cm all mice were sacrificed. Primary tumors and organs were collected for further analysis. Animal studies have been approved by the Institutional Animal Care and Use Committee.

Patient Samples

Patients with metastatic melanoma harboring the BRAF (V600E) mutation (confirmed by genotyping) were enrolled in clinical trials with the BRAF-I (vemurafenib) or with BRAF-I (dabrafenib) and MEK-I (trametinib). Patients were consented for tissue acquisition per IRB-approved protocol. Tumor biopsies were performed pre-treatment (day 0), at 10-14 days on treatment, and/or at the time of disease progression [as defined by Response Evaluation Criteria In Solid Tumors (RECIST)] if applicable. Formalin-fixed tissue was analyzed to confirm that viable tumor was present via hematoxylin and eosin (H&E) staining Immunohistochemistry and Immunofluorescence Patient biopsies and tumors generated in mice were formalin fixed and paraffin embedded and then used as substrates in immunohistochemical reactions. Five-um thick xenograft tissue sections were fixed on silane-coated glass slides, deparaffinized, and subjected to antigen retrieval (Target retrieval solution, DAKO). Following blocking, slides from mice were incubated with Cleaved Caspase-3 (Asp175) and p-Histone H3 (Ser10)—specific mAbs overnight. Four-um thick sections from patient-derived samples were incubated with PDGFRα-specific mAb (sc-338, Santa Cruz) (1:400) overnight. Sections were then washed with PBS, and the primary antibody was amplified using the VECTASTAIN ABC Kit (Peroxidase rabbit IgG, Vector Laboratories, PK-4001). The detection of this antibody was performed with the DAB Peroxidase Substrate Kit from DAKO and the sections were counterstained with H&E. PDGFRα expression, as measured by its staining intensity, in tumors harvested from BRAF-I treated patients either on treatment or at the time of disease progression was compared to that the staining in pretreatment tumors. Scores were recorded semiquantitatively as 1+, 2+, 3+ and 4+, when, 1-25%, 26-50%, 51-75% and >75% of cells were stained, respectively. Mitotic and apoptotic tumor cells in the sections of primary tumors harvested from mice were detected by staining p-Histone H3 (Ser10) and Cleaved Caspase-3 proteins, respectively, and quantified by counting 5 random fields per section (magnification ×200). Data were expressed as the mean number of mitotic or apoptotic tumor cells in each group. The number of mitotic or apoptotic tumor cells was counted by an investigator who was blinded to the type of treatment received by the mice from which tumors had been harvested.

Statistical Analysis

Averages, standard deviations, and unpaired t-test were calculated using MS-Excel. Data showed the mean±SD of the results obtained in at least three independent experiments. Time of disease progression (time to progression) of BRAF-I treated patients was calculated using the Kaplan-Meier methods. Differences between groups were considered significant when the P value was <0.05. The asterisk (*) indicates P<0.05.

References for Materials and Methods

1. Ogino, T., et al. Endoplasmic reticulum chaperone-specific monoclonal antibodies for flow cytometry and immunohistochemical staining *Tissue antigens* 62, 385-393 (2003).

2. Yu, L., et al. The CSPG4-specific monoclonal antibody enhances and prolongs the effects of the BRAF inhibitor in melanoma cells. *Immunol Res* 50, 294-302 (2011).

3. Wang, X., et al. CSPG4 protein as a new target for the antibody-based immunotherapy of triple-negative breast cancer. *J Natl Cancer Inst* 102, 1496-1512 (2010).

4. Tang, J. B., et al. Bioenergetic metabolites regulate base excision repair-dependent cell death in response to DNA damage. *Molecular cancer research: MCR* 8, 67-79 (2010).

5. Vermes, I., Haanen, C., Steffens-Nakken, H. & Reutelingsperger, C. A novel assay for apoptosis. Flow cytometric detection of phosphatidylserine expression on early apoptotic cells using fluorescein labelled Annexin V. *Journal of immunological methods* 184, 39-51 (1995).

6. Yang, H., et al. RG7204 (PLX4032), a selective BRAFV600E inhibitor, displays potent antitumor activity in preclinical melanoma models. *Cancer research* 70, 5518-5527 (2010).

7. Chow, L. Q. & Eckhardt, S. G. Sunitinib: from rational design to clinical efficacy. *Journal of clinical oncology: official journal of the American Society of Clinical Oncology* 25, 884-896 (2007).

8. Buchdunger, E., et al. Inhibition of the Abl protein-tyrosine kinase in vitro and in vivo by a 2-phenylaminopyrimidine derivative. *Cancer research* 56, 100-104 (1996).

Example 1. Sonic Hedgehog Pathway Activation and BRAF Inhibitor Resistance

Control of mutant BRAF(V600E) metastatic melanoma by the selective BRAF inhibitor (BRAF-I) is limited by intrinsic and acquired resistance. We demonstrate for the first time that PDGFRα upregulation causes BRAF-I resistance in vitro and in vivo. PDGFRα inhibition by PDGFRα-specific shRNA and by PDGFRα inhibitors restores melanoma cells' sensitivity to BRAF-I in vitro and in vivo. PDGFRα inhibition reverses ERK and AKT mediated proliferation and resistance to apoptosis which are associated with BRAF-I resistance. PDGFRα upregulation is mediated by activation of the Sonic Hedgehog Homolog (SHH) pathway which is induced by BRAF-I treatment. PDGFRα upregulation is found in melanoma matched biopsies of BRAF-I treated patients and correlates with shorter time to disease progression and less tumor regression. These data suggest that monitoring patients for early PDGFRα upregulation may identify those who may most benefit from the treatment with vemurafenib in combination with PDGFRα inhibitors or SHH inhibitor utilizing currently available agents.

1A. ERK Reactivation, AKT Activation and PDGFRα Upregulation in Colo38R, M21R and TPF-10-741 Melanoma Cell Lines with Acquired Vemurafenib Resistance To assess the BRAF-I sensitivity of the parental Colo38 and M21 cell lines and those with acquired BRAF-I resistance Colo38R, M21R and TPF-10-741, growth inhibition was analyzed following treatment with vemurafenib. MTT assays demonstrated that Colo38 and M21 cells were exquisitely sensitive to the anti-proliferative activity of vemurafenib, while Colo38R and M21R cells had acquired resistance to the growth inhibitory effects of vemurafenib. TPF-10-741 cells displayed an intermediate sensitivity to vemurafenib (FIG. 7). This acquired resistance model was used to investigate the molecular mechanisms underlying disease progression after an initial response to vemurafenib. Since acquired vemurafenib resistance can be mediated by reactivation of the RAF/MEK/ERK pathway or by activation of alternative pathways like PI3K/AKT, signaling through these pathways were evaluated in both parental and resistant cell lines (FIG. 1A). Western blot analysis demonstrated that following incubation with vemurafenib p-ERK levels were reduced in both Colo38 and M21 cells, but no change in p-ERK levels was detected in Colo38R and M21R cells. A limited effect on TPF-10-741 cells was seen. p-AKT levels were increased in Colo38R and M21R cells compared to Colo38 and M21 cells. P-AKT levels also increased in M21 and TPF-10-741 cells after treatment with BRAF-I. Therefore the decreased sensitivity to the inhibition of the RAF/MEK/ERK pathway by BRAF-I was associated with the reactivation of the RAF/MEK/ERK pathway and with activation of AKT.

Since BRAF-I resistance through activation of the PI3K/AKT pathway can be mediated by RTK upregulation[14], we investigated the role of RTK in acquired vemurafenib resistance. Western blot analysis (FIG. 1B) demonstrated that treatment with vemurafenib enhanced PDGFRα activation and expression in Colo38R and M21R cells as compared to the parental cells. PDGFRα was also expressed and activated in TPF-10-741 cells both under basal conditions and following treatment with vemurafenib. PDGFRβ was upregulated on TPF-10-741 cells after treatment with vemurafenib, but not in the other cell lines. VEGFR2 expression was not detected in any cell lines before or after treatment with vemurafenib. Further analysis of the RAF/MEK/ERK and PI3K/AKT pathway components demonstrated that PDGFRα upregulation was associated with PI3K, CRAF and MEK activation in Colo38R, M21R, and TPF-10-741 cells. Lastly, analysis of PTEN status demonstrated the lack of its expression in TPF-10-741 cells, but not in the other cells.

1B. PDGFRα Mediates Acquired Vemurafenib Resistance in Colo38R, M21R, and TPF-10-741 Melanoma Cell Lines by Reactivation of the RAS/RAF/ERK Pathway and Activation of the PI3K/AKT Pathway To test whether PDGFRα upregulation resulted in vemurafenib resistance in Colo38R, M21R and TPF-10-741, PDGFRα was knocked down in the three cell lines using 5 PDGFRα-specific shRNAs. As shown in FIG. 2A, lentiviral transduction of M21R cells with a PDGFRα-specific shRNA(#4) construct knocked down PDGFRα protein expression. PDGFRα downregulation was associated with decreased p-ERK and p-AKT. Additionally, the M21R and TPF-10-741 cells transduced with the PDGFRα-specific shRNA(#4) displayed a significantly increased sensitivity to vemurafenib, as compared to the autologous cells transduced with a GFP-shRNA (P<0.01) (FIG. 2B). Lastly, western blot analysis demonstrated that the PDGFRα downregulation caused by the PDGFRα-specific shRNA(#4) in combination with vemurafenib treatment dramatically decreased the levels of p-ERK and p-AKT in M21R cells (FIG. 2A).

1C. Association of PDGFRα Upregulation in Melanoma Patient Derived Biopsies with BRAF-I Resistance To validate our in vitro findings we compared PDGFRα expression in biopsies obtained from 9 melanoma patients treated with BRAF-I+/−MEK-I (Table 1). Tumor biopsies were performed before treatment, on treatment, and at the time of disease progression. Immunohistochemical staining demonstrated PDGFRα upregulation in 5 out of 9 patients following treatment with BRAF-I+/−MEK-I (FIG. 3A). Interestingly, in 3 of the 5 patients a significant increase in PDGFRα expression (>1+) was observed after treatment. Patients with a significant (>1+) increase in PDGFRα expression after treatment with BRAF-I+/−MEK-I had less tumor regression based on RECIST criteria (FIG. 3B) and shorter time to disease progression (FIG. 3C) when compared to patients who had no change or a small change in expression (≤1+).

| ID# | Sex | Age | Treatment | Objective Response | time to progression (months) | PDGFRα IHC Expression Score (+) | | |
|---|---|---|---|---|---|---|---|---|
| | | | | | | Pre-treatment | On-treatment | After Progression of disease |
| 1 | M | 68 | BRAFi | SD (−25%) | 5 | 1 | 3 | — |
| 7 | M | 56 | BRAFi + ivEKi | CR (100%) | 17 | 1 | — | 2 |
| 8 | M | 37 | BRAFi + ivEKi | PR (−30%) | 3 | 4 | 4 | — |
| 10 | F | 37 | BRAFi + ivEKi | SD (−13%) | 3 | 0 | 4 | — |
| 12 | F | 31 | BRAFi + ivEKi | PR (−88.9%) | 12 | 3 | 3 | — |
| 13 | M | 89 | BRAFi + ivEKi | PR (−57.9%) | 9 | 1 | 2 | — |
| 17 | M | 74 | BRAFi | PR (−71.7) | 15 | — | — | 1 |
| 21 | M | 61 | BRAFi + ivEKi | PR (−49%) | 13 | — | — | 4 |
| 25 | M | 72 | BRAFi + ivEKi | PR (−64%) | 3 | 1 | — | 4 |

1D. Inhibition of PDGFRα Increases the Anti-Tumor Activity of Vemurafenib in BRAF-I Sensitive and Resistant Melanoma Cell Lines To investigate whether the anti-tumor activity of BRAF-I could be enhanced by PDGFRα inhibition, Colo38, Colo38R, M21, M21R and TPF-10-741 cells were treated with vemurafenib and/or PDGFRα-I sunitinib[21] or imatinib[22] or crenolanib (Dai et al., 2013, supra). A dose titration experiment established the dose of PDGFRα-I to be combined with vemurafenib in the 5 cell lines. The IC50 doses of sunitinib, imatinib and crenolanib were found to be 2, 15 and 1 μM, respectively (FIG. 8). The dose of 1.5 μM and 3 μM for sunitinib and the dose of 10 μM and 20 μM for imatinib were chosen to be tested in combination with vemurafenib for their effect on cell growth (FIG. 9) and survival (FIG. 10). Cell growth inhibition of Colo38 and M21 by the MTT assay demonstrated that vemurafenib in combination with PDGFRα-I significantly inhibited proliferation (p<0.05) when compared to each agent alone. Furthermore, PDGFRα-I synergized (p<0.05) with vemurafenib to overcome BRAF-I resistance, increasing the growth inhibition of Colo38R, M21R and TPF-10-741 cells. Analysis of apoptosis by the Annexin-V expression assay demonstrated that treatment with vemurafenib and sunitinib induced apoptosis in a significantly (p<0.05) higher percentage of cells than each agent alone in both BRAF-I sensitive and resistant cell lines. Sunitinib, but not vemurafenib resulted in a significantly higher percentage of apoptotic cells in both BRAF-I sensitive and resistant cell lines (p<0.05).

1E. BRAF and PDGFRα Inhibition Leads to Inhibition of ERK and AKT Activation

We next investigated whether vemurafenib in combination with the PDGFRα-I could inhibit ERK and AKT activation in BRAF-I sensitive and resistant cells. Western blot analysis (FIG. 4) demonstrated that p-ERK levels were decreased when Colo38 and M21 cells were treated with vemurafenib, but to a lesser extent with sunitinib. In addition, p-AKT levels were increased when M21 cells were treated with vemurafenib, but reduced when Colo38 and M21 cells were treated with sunitinib. However, vemurafenib in combination with sunitinib strongly inhibited the levels of both p-ERK and p-AKT in both Colo38 and M21 cells. On the other hand, p-ERK levels were not inhibited by the treatment with vemurafenib in Colo38R, M21R, or TPF-10-741 cells. Treatment with sunitinib minimally inhibited p-ERK levels in Colo38R, M21R and TPF-10-741 cells, but reduced p-AKT levels in Colo38R and TPF-10-741 cells. However, the combination of vemurafenib with sunitinib inhibited both p-ERK and p-AKT levels to a greater extent than each agent alone in all of the BRAF-I resistant cell lines. Similar results were obtained with vemurafenib in combination with imatinib (FIG. 4).

1F. Melanoma Xenograft Growth Inhibition by the Combination of Vemurafenib and PDGFRα-I To assess the in vivo relevance of our in vitro results, the combination of vemurafenib and the PDGFRα-I sunitinib or imatinib were tested for the ability to inhibit the growth of M21 and M21R cells in SCID mice. The oral administration of the drugs caused no overt side effects. In the mice grafted with the M21 cells (FIG. 5A) treatment with vemurafenib (12.5 mg/kg twice daily) or sunitinib (20 mg/kg daily) significantly (p<0.001) inhibited tumor growth as compared to untreated mice. However, vemurafenib in combination with sunitinib inhibited tumor growth to a significantly (p<0.001) greater extent than each single agent. Similar results were obtained combining vemurafenib (25 mg/kg twice daily) with imatinib (100 mg/kg daily) (FIG. 11). Western blot analysis of the tumor lysates removed from treated and untreated mice (FIG. 5B) demonstrated that vemurafenib decreased p-ERK levels but increased p-AKT levels, while sunitinib decreased p-ERK and p-AKT levels. This effect was more marked in tumors from mice treated with vemurafenib in combination with sunitinib. Analysis of primary tumors by IHC demonstrated that vemurafenib in combination with sunitinib (FIG. 5C) markedly reduced the number of mitotic cells in tumors when compared to tumors from untreated mice (p<0.001) or mice treated with the single agents (p<0.001). The number of apoptotic cells (FIG. 5D) in tumors from mice treated with vemurafenib and sunitinib was significantly higher than in tumors from untreated mice or from mice treated with vemurafenib or sunitinib individually (p<0.001). Sunitinib, but not vemurafenib resulted in a significantly higher number of apoptotic cells in the tumors when compared to untreated mice (p<0.001).

In the mice grafted with the M21R cells (FIG. 5E) vemurafenib did not inhibit tumor growth as compared to untreated mice. In contrast, sunitinib caused a significant inhibition of tumor growth compared to untreated mice (p<0.001). Vemurafenib in combination with sunitinib inhibited tumor growth to a significantly (P<0.001) greater extent than sunitinib alone. Western blot analysis of tumor lysates (FIG. 5F) demonstrated that sunitinib inhibited p-AKT and p-ERK levels. This effect was more marked in tumors from mice treated with vemurafenib in combination with sunitinib. As expected the levels of p-ERK and p-AKT were not affected by treatment with vemurafenib as a single agent. IHC staining (FIG. 5G) revealed that treatment with sunitinib markedly decreased the number of mitotic cells in tumors as compared to that in tumors from vemurafenib or untreated mice (p<0.001). In addition, treatment with sunitinib caused a strong increase in the number of apoptotic cells in tumors as compared to tumors from vemurafenib treated or untreated mice (p<0.001) (FIG. 5H). However treatment with vemurafenib in combination with sunitinib decreased the number of mitotic cells and increased the number of apoptotic cells to a significantly (p<0.001) greater extent than treatment with sunitinib alone.

1G. SHH Pathway Activation Mediates BRAF-I Resistance by PDGFRα Upregulation

Figure 6A:
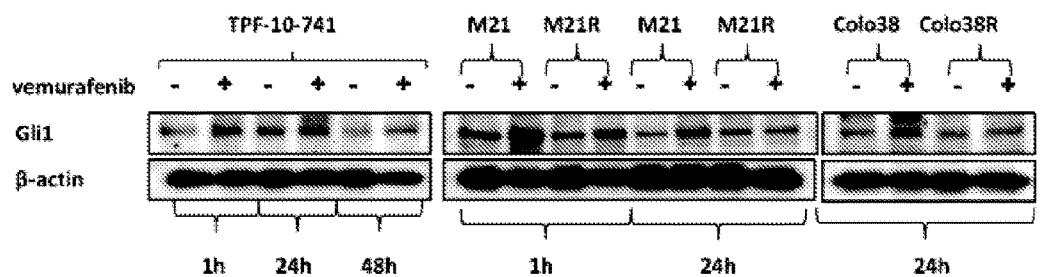
Figure 6B:
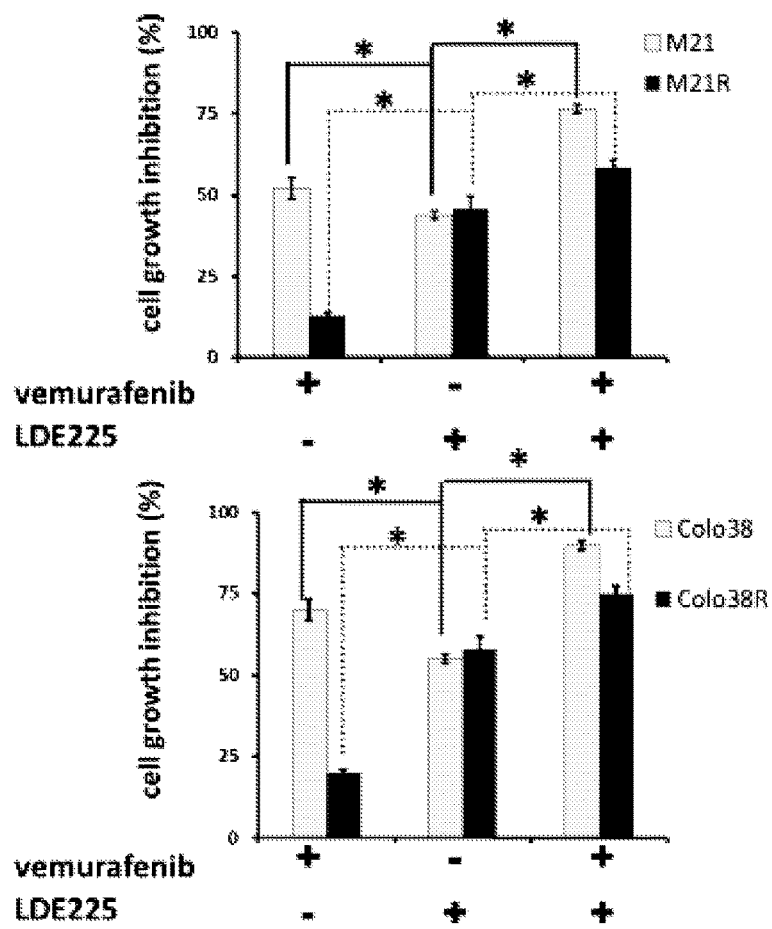
Figure 6C:
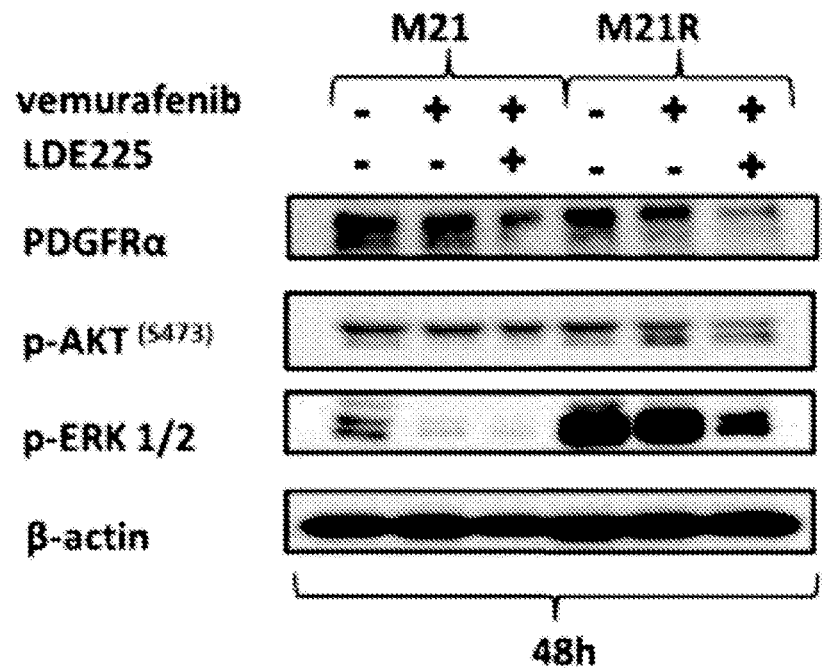
Figure 6D:
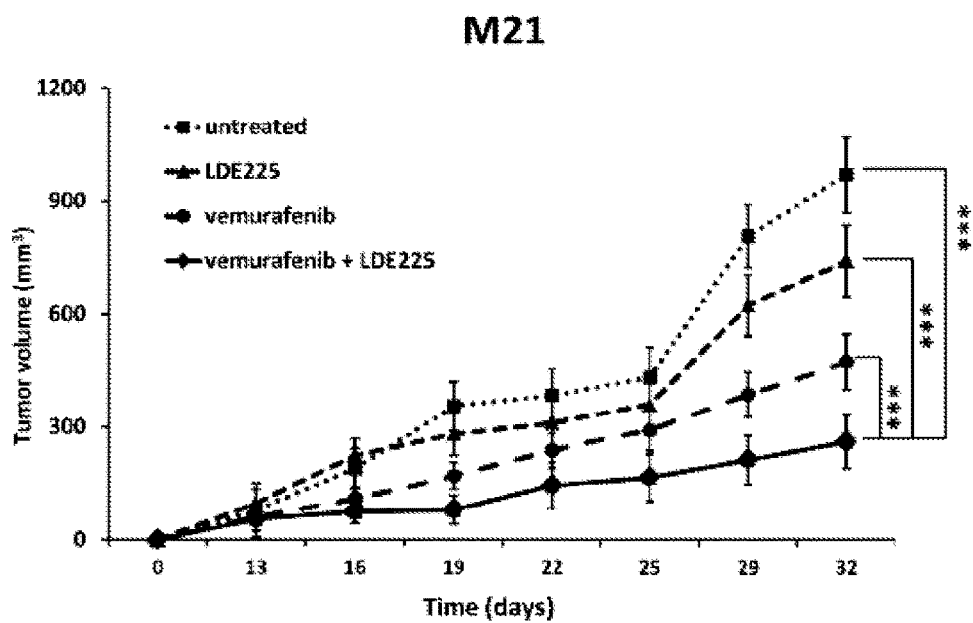

The previously described role of the SHH pathway and Gli1 activation[23-26] in the PDGFRα upregulation associated with MAPK pathway activation prompted us to investigate whether Gli1 activation is involved in PDGFRα upregulation which in turn mediates BRAF-I resistance. Western blot analysis (FIG. 6A) demonstrated that treatment with vemurafenib enhanced Gli1 expression in Colo38, Colo38R, M21, M21R, and TPF-10-741 cells as compared to untreated cells. The association between Gli1 expression and PDGFRα upregulation mediating BRAF-I resistance was also indicated by the marked inhibition of tumor growth (p<0.05) both in vitro and in vivo and expression level of PDGFRα, p-ERK and p-AKT in the BRAF-I sensitive and resistant cells after treatment with both vemurafenib and LDE225, a novel SHH-I[27] (FIGS. 6B-6D).

References for Detailed Description and Example 1

1. Brose, M. S., et al. BRAF and RAS mutations in human lung cancer and melanoma. Cancer research 62, 6997-7000 (2002).

2. Long, G. V., et al. Prognostic and clinicopathologic associations of oncogenic BRAF in metastatic melanoma. J Clin Oncol 29, 1239-1246 (2011).

3. Wan, P. T., et al. Mechanism of activation of the RAF-ERK signaling pathway by oncogenic mutations of B-RAF. Cell 116, 855-867 (2004).

4. Karasarides, M., et al. B-RAF is a therapeutic target in melanoma. Oncogene 23, 6292-6298 (2004).

5. Cohen, C., et al. Mitogen-actived protein kinase activation is an early event in melanoma progression. Clin Cancer Res 8, 3728-3733 (2002).

6. Lopez-Bergami, P. The role of mitogen- and stress-activated protein kinase pathways in melanoma. Pigment Cell Melanoma Res 24, 902-921 (2011).

7. Flaherty, K. T., et al Inhibition of mutated, activated BRAF in metastatic melanoma. The New England journal of medicine 363, 809-819 (2010).

8. Chapman, P. B., et al. Improved survival with vemurafenib in melanoma with BRAF V600E mutation. N Engl J Med 364, 2507-2516 (2011).

9. Sosman, J. A., et al. A phase 2 trial of complete resection for stage IV melanoma: Results of Southwest Oncology Group Clinical Trial S9430. Cancer (2011).

10. Emery, C. M., et al. MEK1 mutations confer resistance to MEK and B-RAF inhibition. Proc Natl Acad Sci USA 106, 20411-20416 (2009).

11. Wagle, N., et al. Dissecting therapeutic resistance to RAF inhibition in melanoma by tumor genomic profiling. Journal of clinical oncology: official journal of the American Society of Clinical Oncology 29, 3085-3096 (2011).

12. Corcoran, R. B., et al. BRAF gene amplification can promote acquired resistance to MEK inhibitors in cancer cells harboring the BRAF V600E mutation. Science signaling 3, ra84 (2010).

13. Montagut, C., et al. Elevated CRAF as a potential mechanism of acquired resistance to BRAF inhibition in melanoma. Cancer research 68, 4853-4861 (2008).

14. Nazarian, R., et al. Melanomas acquire resistance to B-RAF(V600E) inhibition by RTK or N-RAS upregulation. Nature 468, 973-977 (2010).

15. Johannessen, C. M., et al. COT drives resistance to RAF inhibition through MAP kinase pathway reactivation. Nature 468, 968-972 (2010).

16. Poulikakos, P. I., et al. RAF inhibitor resistance is mediated by dimerization of aberrantly spliced BRAF (V600E). Nature 480, 387-390 (2011).

17. Shi, H., Kong, X., Ribas, A. & Lo, R. S. Combinatorial treatments that overcome PDGFRbeta-driven resistance of melanoma cells to V600EB-RAF inhibition. Cancer research 71, 5067-5074 (2011).

18. Villanueva, J., et al. Acquired resistance to BRAF inhibitors mediated by a RAF kinase switch in melanoma can be overcome by cotargeting MEK and IGF-1R/PI3K. Cancer cell 18, 683-695 (2010).

19. Paraiso, K. H., et al. PTEN loss confers BRAF inhibitor resistance to melanoma cells through the suppression of BIM expression. Cancer Res 71, 2750-2760 (2011).

20. Flaherty, K. T., et al. Combined BRAF and MEK inhibition in melanoma with BRAF V600 mutations. The New England journal of medicine 367, 1694-1703 (2012).

21. Chow, L. Q. & Eckhardt, S. G. Sunitinib: from rational design to clinical efficacy. Journal of clinical oncology: official journal of the American Society of Clinical Oncology 25, 884-896 (2007).

22. Buchdunger, E., et al. Inhibition of the Abl protein-tyrosine kinase in vitro and in vivo by a 2-phenylaminopyrimidine derivative. Cancer research 56, 100-104 (1996).

23. Xie, J., et al. A role of PDGFRalpha in basal cell carcinoma proliferation. Proceedings of the National Academy of Sciences of the United States of America 98, 9255-9259 (2001).

24. Ruiz i Altaba, A., Sanchez, P. & Dahmane, N. Gli and hedgehog in cancer: tumours, embryos and stem cells. Nature reviews. Cancer 2, 361-372 (2002).

25. Stecca, B., et al. Melanomas require HEDGEHOG-GLI signaling regulated by interactions between GLI1 and the RAS-MEK/AKT pathways.

Proceedings of the National Academy of Sciences of the United States of America 104, 5895-5900 (2007).

26. Ruiz i Altaba, A., Mas, C. & Stecca, B. The Gli code: an information nexus regulating cell fate, sternness and cancer. Trends in cell biology 17, 438-447 (2007).

27. Fendrich, V., et al. Hedgehog inhibition with the orally bioavailable Smo antagonist LDE225 represses tumor growth and prolongs survival in a transgenic mouse model of islet cell neoplasms Annals of surgery 254, 818-823; discussion 823 (2011).

28. Andrae, J., Gallini, R. & Betsholtz, C. Role of platelet-derived growth factors in physiology and medicine. Genes & development 22, 1276-1312 (2008).

29. Agaram, N. P., et al. Novel V600E BRAF mutations in imatinib-naive and imatinib-resistant gastrointestinal stromal tumors. Genes, chromosomes & cancer 47, 853-859 (2008).

30. Agaimy, A., et al. V600E BRAF mutations are alternative early molecular events in a subset of KIT/PDGFRA wild-type gastrointestinal stromal tumours. Journal of clinical pathology 62, 613-616 (2009).

31. Hostein, I., et al. BRAF mutation status in gastrointestinal stromal tumors. American journal of clinical pathology 133, 141-148 (2010).

32. Miranda, C., et al. KRAS and BRAF mutations predict primary resistance to imatinib in gastrointestinal stromal tumors. Clinical cancer research: an official journal of the American Association for Cancer Research 18, 1769-1776 (2012).

33. Straussman, R., et al. Tumour micro-environment elicits innate resistance to RAF inhibitors through HGF secretion. Nature 487, 500-504 (2012).

34. Cheung, M., Sharma, A., Madhunapantula, S. V. & Robertson, G. P. Akt3 and mutant V600E B-Raf cooperate to promote early melanoma development. Cancer research 68, 3429-3439 (2008).

35. Chappell, W. H., et al. Ras/Raf/MEK/ERK and PI3K/PTEN/Akt/mTOR inhibitors: rationale and importance to inhibiting these pathways in human health. Oncotarget 2, 135-164 (2011).

36. Atefi, M., et al. Reversing melanoma cross-resistance to BRAF and MEK inhibitors by co-targeting the AKT/mTOR pathway. PLoS One 6, e28973 (2011).

37. Greger, J. G., et al. Combinations of BRAF, MEK, and PI3K/mTOR inhibitors overcome acquired resistance to the BRAF inhibitor GSK2118436 dabrafenib, mediated by NRAS or MEK mutations. Molecular cancer therapeutics 11, 909-920 (2012).

38. Su, F., et al. Resistance to selective BRAF inhibition can be mediated by modest upstream pathway activation. Cancer Res 72, 969-978 (2012).

39. Deng, W., et al. Role and therapeutic potential of PI3K-mTOR signaling in de novo resistance to BRAF inhibition. Pigment cell & melanoma research 25, 248-258 (2012).

40. Sanchez-Hernandez, I., Baquero, P., Calleros, L. & Chiloeches, A. Dual inhibition of (V600E)BRAF and the PI3K/AKT/mTOR pathway cooperates to induce apoptosis in melanoma cells through a MEK-independent mechanism. Cancer letters 314, 244-255 (2012).

Example 2. Enhancement of the Anti-Tumor Activity of LDE225 by Radiation and Grp94-Specific Monoclonal Antibody Combination Therapy The mAb W9, which we have recently developed, has a unique specificity because it recognizes an extracellular epitope of the heat shock protein (HSP) glucose regulated protein of 94000 daltons (Grp94). Similar to other members of the HSP90 family, the molecular chaperone Grp94 is required for the stability and activity of client proteins involved in the activation of signaling pathways associated with tumor cell survival and proliferation[1-3]. These functional properties of Grp94 provide a molecular mechanism for the anti-proliferative effect and the induction of apoptosis of malignant cells by Grp94 inhibitors[4]. What distinguishes mAb W9 from other Grp94-specific mAbs, described in the literature and/or available commercially, is its ability to selectively target malignant cells by recognizing a carbohydrate epitope that is expressed on malignant cells but is not detectable on normal cells.

Grp94-specif mAb W9 was selected as the target of our combinatorial immunotherapy for the following reasons. First this epitope is expressed in pancreatic ductal adenocarcinoma (PDAC) cell lines and in patient derived PDAC lesions. Second it is expressed at high level not only on differentiated PDAC cells but also on PDAC CICs, defined as cells expressing high level of Aldehyde Dehydrogenases A1 (ALDH$^{bright}$). As a result we will target not only differentiated PDAC cells, but also pancreatic CICs. According to the literature[5-7], and our own unpublished data, ALDH$^{bright}$ cells have the characteristics of CICs, such as self-renewal, chemo- and radio-resistance, aberrant regulation of stem cell signaling pathways (such as SHH and Notch), and high tumorigenicity at low cell numbers in SCID mice[8-10].

To enhance the therapeutic efficacy of Grp94-targeted mAb-based immunotherapy, we will combine it radiation and LDE225 which is currently undergoing clinical evaluation[6]. This small molecule is a novel oral inhibitor of the Sonic Hedgehog Homolog (SHH) pathway[11,12] which is abnormally activated in differentiated PDAC cells and in pancreatic CICs[13-16]. Radiation is a component in the treatment of patients with resectable and locally advanced PDAC. It has been included in our combinatorial strategy, since our preliminary in vitro studies demonstrate that radiation markedly enhances Grp94 expression on PDAC cells. Furthermore, inhibition of the functions and/or expression of Grp94 enhances the sensitivity of tumor cells to radiation[17-19]. These mechanisms provide an explanation for the enhancement by Grp94 specific-mAb W9 of the ability of LDE225 and radiation to eliminate in vitro CICs, detected as ALDH$^{bright}$ cells in PDAC cell lines (p<0.05) (FIG. 12).

References for Example 2

1. Argon Y, Simen B B. Grp94, an er chaperone with protein and peptide binding properties. *Seminars in cell & developmental biology.* 1999; 10:495-505

2. Yang Y, Li Z. Roles of heat shock protein gp96 in the er quality control: Redundant or unique function? *Molecules and cells.* 2005; 20:173-182

3. Pan Z, Erkan M, Streit S, Friess H, Kleeff J. Silencing of grp94 expression promotes apoptosis in pancreatic cancer cells. *International journal of oncology.* 2009; 35:823-828

4. Marzec M, Eletto D, Argon Y. Grp94: An hsp90-like protein specialized for protein folding and quality control in the endoplasmic reticulum. *Biochim Biophys Acta.* 2012; 1823:774-787

5. Li C, Heidt D G, Dalerba P, Burant C F, Zhang L, Adsay V, Wicha M, Clarke M F, Simeone D M. Identification of pancreatic cancer stem cells. *Cancer Res.* 2007; 67:1030-1037

6. Kim M P, Fleming J B, Wang H, Abbruzzese J L, Choi W, Kopetz S, McConkey D J, Evans D B, Gallick G E. Aldh activity selectively defines an enhanced tumor-initiating cell population relative to cd133 expression in human pancreatic adenocarcinoma. *PloS one.* 2011; 6:e20636

7. Rasheed Z A, Matsui W. Biological and clinical relevance of stem cells in pancreatic adenocarcinoma. *Journal of gastroenterology and hepatology.* 2012; 27 Suppl 2:15-18

8. Clarke M F, Dick J E, Dirks P B, Eaves C J, Jamieson C H, Jones D L, Visvader J, Weissman I L, Wahl G M. Cancer stem cells—perspectives on current status and future directions: Aacr workshop on cancer stem cells. *Cancer Res.* 2006; 66:9339-9344

9. Lauth M. Ras and hedgehog—partners in crime. *Frontiers in bioscience: a journal and virtual library.* 2011; 16:2259-2270

10. Visvader J E. Cells of origin in cancer. *Nature.* 2011; 469:314-322

11. Fendrich V, Wiese D, Waldmann J, Lauth M, Heverhagen A E, Rehm J, Bartsch D K. Hedgehog inhibition with the orally bioavailable smo antagonist 1de225 represses tumor growth and prolongs survival in a transgenic mouse model of islet cell neoplasms. *Ann Surg.* 2011; 254:818-823; discussion 823

12. Irvine D A, Copland M. Targeting hedgehog in hematologic malignancy. *Blood.* 2012; 119:2196-2204

13. Olive K P, Jacobetz M A, Davidson C J, Gopinathan A, McIntyre D, Honess D, Madhu B, Goldgraben M A, Caldwell M E, Allard D, Frese K K, Denicola G, Feig C, Combs C, Winter S P, Ireland-Zecchini H, Reichelt S, Howat W J, Chang A, Dhara M, Wang L, Ruckert F, Grutzmann R, Pilarsky C, Izeradjene K, Hingorani S R, Huang P, Davies S E, Plunkett W, Egorin M, Hruban R H, Whitebread N, McGovern K, Adams J, Iacobuzio-Donahue C, Griffiths J, Tuveson D A Inhibition of hedgehog signaling enhances delivery of chemotherapy in a mouse model of pancreatic cancer. *Science.* 2009; 324:1457-1461

14. Kelleher F C. Hedgehog signaling and therapeutics in pancreatic cancer. *Carcinogenesis.* 2011; 32:445-451

15. Quint K, Tonigold M, Di Fazio P, Montalbano R, Lingelbach S, Ruckert F, Alinger B, Ocker M, Neureiter D. Pancreatic cancer cells surviving gemcitabine treatment express markers of stem cell differentiation and epithelial-mesenchymal transition. *International journal of oncology.* 2012

16. Xu X, Zhou Y, Xie C, Wei S M, Gan H, He S, Wang F, Xu L, Lu J, Dai W, He L, Chen P, Wang X, Guo C. Genome-wide screening reveals an emt molecular network mediated by sonic hedgehog-gli1 signaling in pancreatic cancer cells. *PloS one.* 2012; 7:e43119

17. Zhang B, Wang Y, Pang X, Su Y, Ai G, Wang T. Er stress induced by ionising radiation in iec-6 cells. *International journal of radiation biology.* 2010; 86:429-435

18. Akutsu Y, Matsubara H, Urashima M, Komatsu A, Sakata H, Nishimori T, Yoneyama Y, Hoshino I, Murakami K, Usui A, Kano M, Ochiai T. Combination of direct intratumoral administration of dendritic cells and irradiation induces strong systemic antitumor effect mediated by grp94/gp96 against squamous cell carcinoma in mice. *International journal of oncology.* 2007; 31:509-515

19. Liu S, Wang H, Yang Z, Kon T, Zhu J, Cao Y, Li F, Kirkpatrick J, Nicchitta C V, Li CY. Enhancement of cancer radiation therapy by use of adenovirus-mediated secretable glucose-regulated protein 94/gp96 expression. *Cancer Res.* 2005; 65:9126-9131

Example 3. Enhancement of the Anti-Tumor Activity of LDE 225 by CSPG4-Specific Monoclonal Antibodies As noted above, CSPG4 is a good target for combinatorial immunotherapy. As a result, targeting TNBC cells with a CSPG4-specific mAb inhibits their proliferation and metastatic spread in SCID mice by inhibiting ERK and AKT activation, as we have recently described[3].

To enhance the therapeutic efficacy of CSPG4-targeted mAb-based immunotherapy, we will combine it with a novel oral inhibitor (LDE225)[4, 5] of the SHH signaling pathway. This small molecule, which is currently undergoing clinical evaluation[6], has been selected since the SHH pathways is activated in TNBC cells and especially in TNBC CICs[7, 8]. Furthermore there is evidence that SHH pathway can cross talk with MAPK and PI3K/AKT pathways which are both inhibited by CSPG4-specific mAbs[9-11]. These mechanisms provide an explanation for the enhancement by CSPG4 specific-mAb 225.28 of the ability of LDE225 to eliminate in vitro CICs, detected as ALDH$^{bright}$ cells in TNBC cell lines ($p<0.05$) (FIG. 1).

References for Example 3

3. Wang X, et al. Cspg4 protein as a new target for the antibody-based immunotherapy of triple-negative breast cancer. Journal of the National Cancer Institute. 2010; 102:1496-1512.
4. Fendrich V, et al. Hedgehog inhibition with the orally bioavailable smo antagonist lde225 represses tumor growth and prolongs survival in a transgenic mouse model of islet cell neoplasms. Annals of surgery. 2011; 254:818-823; discussion 823.
5. Pan. S, et al. Discovery of nvp-lde225, a potent and selective smoothened antagonist. ACS Med. Chem. Lett. 2010; 1:130-134.
6. Irvine D A, and Copland M. Targeting hedgehog in hematologic malignancy. Blood. 2012; 119:2196-2204.
7. Tao Y, et al. Overexpression of hedgehog signaling molecules and its involvement in triple-negative breast cancer. Oncology letters. 2011; 2:995-1001.
8. Kameda C, et al. The hedgehog pathway is a possible therapeutic target for patients with estrogen receptor-negative breast cancer. Anticancer research. 2009; 29:871-879.
9. Elia D, et al. Sonic hedgehog promotes proliferation and differentiation of adult muscle cells: Involvement of mapk/erk and pi3k/akt pathways. Biochimica et biophysica acta. 2007; 1773:1438-1446.
10. Ji Z, et al. Oncogenic kras activates hedgehog signaling pathway in pancreatic cancer cells. The Journal of biological chemistry. 2007; 282:14048-14055.
11. Dormoy V, et al. The sonic hedgehog signaling pathway is reactivated in human renal cell carcinoma and plays orchestral role in tumor growth. Molecular cancer. 2009; 8:123.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for treating a BRAF inhibitor (BRAF-I)-resistant cancer, the method comprising the steps of:
   a. identifying a subject who has an increase in a level of PDGFRα in a biopsy sample collected from the subject after treatment with the BRAF-I as compared with a level of PDGFRα before treatment, wherein the BRAF-I is Vemurafenib, GDC-0879, PLX-4720, GSK2118436, Sorafenib Tosylate, dabrafenib, or LGX818; and
   b. administering a therapeutically effective amount of the BRAF-I and an inhibitor selected from the group consisting of TAK-441, itraconazole, and erismodegib to the subject,
   thereby treating the BRAF-I-resistant cancer.

2. The method of claim 1, wherein the BRAF-I-resistant cancer is a melanoma, colon cancer, thyroid cancer, pancreatic adenocarcinoma, triple negative breast cancer, glioma, or sarcoma.

3. The method of claim 1, wherein identifying a subject who has an increase in a level of PDGFRα in a biopsy sample collected from the subject after treatment with the BRAF-I as compared with a level of PDGFRα before treatment comprises:
   (i) obtaining a first biopsy sample from the subject before treatment;
   (ii) determining a level of PDGFRα in the first sample;
   (iii) obtaining a second biopsy sample from the subject after treatment;
   (iv) determining a level of PDGFRα in the second sample;
   (v) comparing the level of PDGFRα in the first sample to the level of PDGFRα in the second sample; and
   (vi) identifying a subject who has an increase in a level of PDGFRα in the second sample as compared with a level of PDGFRα in the first sample.

* * * * *

UNITED STATES PATENT AND TRADEMARK OFFICE
CERTIFICATE OF CORRECTION

PATENT NO. : 10,220,091 B2
APPLICATION NO. : 14/782260
DATED : March 5, 2019
INVENTOR(S) : Francesco Sabbatino et al.

Page 1 of 1

It is certified that error appears in the above-identified patent and that said Letters Patent is hereby corrected as shown below:

In the Specification

In Column 1, Line 6 (approx.), after "This" delete "application"

Signed and Sealed this
Third Day of September, 2019

Andrei Iancu
*Director of the United States Patent and Trademark Office*

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: shRNA target sequence

<400> SEQUENCE: 1
ccagcctcat ataagaagaa a                                       21

<210> SEQ ID NO 2
<211> LENGTH: 21
<212> TYPE: DNA
<213> ORGANISM: Artificial Sequence
<220> FEATURE:
<223> OTHER INFORMATION: shRNA target sequence

<400> SEQUENCE: 2
ccagctttca ttaccctcta t                                       21

<210> SEQ ID NO 3
<211> LENGTH: 20
<212> TYPE: DNA
<213> ORGANISM: Artificial Sequence
<220> FEATURE:
<223> OTHER INFORMATION: shRNA target sequence

<400> SEQUENCE: 3
cggtgaaaga cagtggagat                                         20

<210> SEQ ID NO 4
<211> LENGTH: 21
<212> TYPE: DNA

```
<213> ORGANISM: Artificial Sequence
<220> FEATURE:
<223> OTHER INFORMATION: shRNA target sequence

<400> SEQUENCE: 4
cccaactttc ttatccaact t                                              21

<210> SEQ ID NO 5
<211> LENGTH: 21
<212> TYPE: DNA
<213> ORGANISM: Artificial Sequence
<220> FEATURE:
<223> OTHER INFORMATION: shRNA target sequence

<400> SEQUENCE: 5
caatggactt accctggaga a                                              21
```